(12) United States Patent
Hsueh et al.

(10) Patent No.: US 12,311,127 B2
(45) Date of Patent: May 27, 2025

(54) RADIAL AND TRANS-ENDOCARDIAL DELIVERY CATHETER

(71) Applicant: BioCardia, Inc., Sunnyvale, CA (US)

(72) Inventors: Wai Hsueh, Newark, CA (US); Olin Jay Palmer, San Carlos, CA (US); Scott Comiso, Menlo Park, CA (US); James B. Ross, Livermore, CA (US); Ken Vien, San Jose, CA (US); Julio Argentieri, Buenos Aires (AR); Peter Altman, Menlo Park, CA (US)

(73) Assignee: BioCardia Inc., Sunnyvale, CA (US)

( * ) Notice: Subject to any disclaimer, the term of this patent is extended or adjusted under 35 U.S.C. 154(b) by 309 days.

(21) Appl. No.: 17/831,189

(22) Filed: Jun. 2, 2022

(65) Prior Publication Data

US 2022/0305237 A1     Sep. 29, 2022

Related U.S. Application Data

(60) Continuation of application No. 17/010,603, filed on Sep. 2, 2020, now Pat. No. 11,986,611, which is a
(Continued)

(51) Int. Cl.
*A61M 25/06* (2006.01)
*A61M 25/00* (2006.01)
(Continued)

(52) U.S. Cl.
CPC .... *A61M 25/0606* (2013.01); *A61M 25/0084* (2013.01); *A61M 25/09* (2013.01);
(Continued)

(58) Field of Classification Search
None
See application file for complete search history.

(56) References Cited

U.S. PATENT DOCUMENTS

| 5,183,470 A | 2/1993 | Wettermann |
| 5,228,441 A | 7/1993 | Lundquist |

(Continued)

FOREIGN PATENT DOCUMENTS

| JP | 2000166863 A | 6/2000 |
| JP | 2001501846 A | 2/2001 |

(Continued)

OTHER PUBLICATIONS

Kolewe, et al. Characterization of Aggregate Size in Taxus Suspension Cell Culture. Plant Cell Rep. May 2010; 29(5): 485-494.
(Continued)

*Primary Examiner* — Manuel A Mendez
(74) *Attorney, Agent, or Firm* — Wilson Sonsini Goodrich & Rosati

(57) ABSTRACT

A needle-injection catheter includes a catheter body having a distal end, a proximal end, a stiff proximal portion, a flexible distal portion, and a delivery lumen extending therethrough. In a first embodiment, a straight injection needle extends coaxially from a distal tip of the flexible portion of the catheter body, and a plurality of penetration limiting elements positioned circumferentially about a base of the straight injection needle and configured to fold radially inwardly against a shaft of the needle when constrained in a tubular lumen and to extend radially outwardly when unconstrained. In a second embodiment, a helical needle extends from the distal tip of the flexible portion of the catheter body. The helical needle has at least one helical delivery lumen connected to receive an injectable substance from the delivery lumen of the catheter body.

29 Claims, 23 Drawing Sheets

Related U.S. Application Data continuation of application No. 16/059,480, filed on Aug. 9, 2018, now Pat. No. 10,780,248, which is a division of application No. 14/501,635, filed on Sep. 30, 2014, now Pat. No. 10,071,226.

(60) Provisional application No. 61/884,834, filed on Sep. 30, 2013.

(51) Int. Cl.
*A61M 25/09* (2006.01)
*A61B 17/00* (2006.01)
*A61B 90/00* (2016.01)

(52) U.S. Cl.
CPC ............... *A61B 2017/00247* (2013.01); *A61B 2090/036* (2016.02); *A61M 2025/0089* (2013.01); *A61M 2025/09166* (2013.01); *A61M 2025/09175* (2013.01); *A61M 2025/09191* (2013.01)

(56) References Cited

U.S. PATENT DOCUMENTS

| | | | |
|---|---|---|---|
| 5,243,167 A | 9/1993 | Lundquist et al. | |
| 5,261,889 A | 11/1993 | Laine et al. | |
| 5,322,064 A | 6/1994 | Lundquist | |
| 5,329,923 A | 7/1994 | Lundquist | |
| 5,334,145 A | 8/1994 | Lundquist et al. | |
| 5,405,376 A | 4/1995 | Mulier et al. | |
| 5,454,787 A | 10/1995 | Lundquist | |
| 5,477,856 A | 12/1995 | Lundquist | |
| 5,571,161 A | 11/1996 | Starksen | |
| 5,685,868 A | 11/1997 | Lundquist | |
| 5,851,226 A | 12/1998 | Skubitz et al. | |
| 6,039,727 A | 3/2000 | Javier, Jr. et al. | |
| 6,159,195 A | 12/2000 | Ha et al. | |
| 6,322,548 B1 | 11/2001 | Payne et al. | |
| 6,567,705 B1 * | 5/2003 | Stokes ................ | A61N 1/0575 607/120 |
| 6,582,400 B1 | 6/2003 | Hawk et al. | |
| 6,723,082 B1 | 4/2004 | Payne et al. | |
| 7,402,151 B2 | 7/2008 | Rosenman et al. | |
| 7,635,353 B2 * | 12/2009 | Gurusamy .......... | A61M 25/065 604/170.03 |
| 7,691,086 B2 | 4/2010 | Tekbuchava et al. | |
| 7,736,346 B2 | 6/2010 | Miller et al. | |
| 7,803,136 B2 | 9/2010 | Schatz | |
| 7,840,261 B2 | 11/2010 | Rosenman et al. | |
| 7,840,264 B1 | 11/2010 | Mower | |
| 7,918,819 B2 | 4/2011 | Karmarkar et al. | |
| 7,972,323 B1 | 7/2011 | Bencini et al. | |
| 8,337,518 B2 | 12/2012 | Nance et al. | |
| 8,361,039 B2 | 1/2013 | Schatz | |
| 8,414,558 B2 | 4/2013 | Schatz | |
| 10,071,226 B2 | 9/2018 | Hsueh et al. | |
| 10,780,248 B2 | 9/2020 | Hsueh et al. | |
| 2002/0082584 A1 | 6/2002 | Rosenman et al. | |
| 2003/0009145 A1* | 1/2003 | Struijker-Boudier | ..... A61P 9/00 604/500 |
| 2004/0122456 A1 | 6/2004 | Saadat et al. | |
| 2007/0005018 A1 | 1/2007 | Tekbuchava | |
| 2007/0038225 A1 | 2/2007 | Osborne | |
| 2008/0287918 A1 | 11/2008 | Rosenman et al. | |
| 2009/0177152 A1 | 7/2009 | Altman | |
| 2010/0056989 A1 | 3/2010 | McKay | |
| 2010/0145306 A1 | 6/2010 | Mickley et al. | |
| 2010/0168713 A1 | 7/2010 | Tkebuchava | |
| 2010/0191222 A1 | 7/2010 | Schatz | |
| 2010/0274129 A1 | 10/2010 | Hooven | |
| 2012/0123327 A1 | 5/2012 | Miller | |
| 2020/0398029 A1 | 12/2020 | Hsueh et al. | |

FOREIGN PATENT DOCUMENTS

| | | |
|---|---|---|
| JP | 2002509746 A | 4/2002 |
| JP | 2003529409 A | 10/2003 |
| JP | 2010535583 A | 11/2010 |
| JP | 2011083596 A | 4/2011 |
| WO | WO-9949773 A2 | 10/1999 |
| WO | WO-0126706 A2 | 4/2001 |
| WO | WO-03063942 A1 | 8/2003 |
| WO | WO-2005032637 A2 | 4/2005 |
| WO | WO-2006074159 A2 | 7/2006 |
| WO | WO-2015048795 A2 | 4/2015 |

OTHER PUBLICATIONS

U.S. Appl. No. 17/010,603 Office Action dated Jul. 7, 2023.
Cardiac Interventions Today Apr. 2011, vol. 5, No. 2.
European search report and search opinion dated May 11, 2017 for EP Application No. 14848948.7.
International search report and written opinion dated Mar. 25, 2015 for PCT/US2014/058439.
Meagher, et al. Stresses from flexure in composite helical implantable leads. Med Eng Phys. Oct. 1997;19(7):668-73.
Office action dated Oct. 20, 2017 for U.S. Appl. No. 14/501,635.
Saito, et al. Influence of the ratio between radial artery inner diameter and sheath outer diameter on radial artery flow after transradial coronary intervention. Catheter Cardiovasc Interv. Feb. 1999;46(2):173-8.
U.S. Appl. No. 14/501,635 Notice of Allowance dated May 10, 2018.
U.S. Appl. No. 16/059,480 Notice of Allowance dated Jun. 24, 2020.
U.S. Appl. No. 16/059,480 Office Action dated Dec. 9, 2019.
U.S. Appl. No. 17/010,603 Notice of Allowance dated Jan. 31, 2024.

* cited by examiner

RADIAL AND TRANS-ENDOCARDIAL DELIVERY CATHETER

CROSS-REFERENCE TO RELATED APPLICATIONS

This application is a continuation of U.S. patent application Ser. No. 17/010,603, filed Sep. 2, 2020, which is a continuation of U.S. patent application Ser. No. 16/059,480, filed Aug. 9, 2018, now U.S. Pat. No. 10,780,248, which is a divisional of U.S. patent application Ser. No. 14/501,635, filed Sep. 30, 2014, now U.S. Pat. No. 10,071,226, which claims the benefit of U.S. Provisional Application No. 61/884,834, filed Sep. 30, 2013, the entire content of each of which are incorporated herein by reference.

BACKGROUND OF THE INVENTION

1. Field of the Invention. The present invention relates generally to medical methods and systems. More particularly, the present invention relates to medical methods and systems suitable for substance delivery to the heart via a radial artery and for the intracardiac delivery of cellular aggregates and other agglomerated materials.

Currently, local biotherapeutic delivery to the heart is under clinical investigation for the treatment of acute myocardial infarction, chronic myocardial ischemia, ischemic heart failure, and nonischemic heart failure. The leading paradigm of intramyocardial delivery is trans-endocardial delivery.

Currently available delivery systems include the Myostar® catheter, manufactured by Johnson and Johnson Biological Delivery Systems, Diamond Bar, California, and the BioCardia® Helical Infusion System, manufactured by BioCardia, Inc., San Carlos, California, the assignee of the present invention. Both these systems utilize an 8 French introducer placed through a femoral artery. Both systems have flexible distal portions that are deflectable (steerable) from a proximal handle location, and the BioCardia system includes a centrally located catheter that may be advanced from the introducer to extend to the heart wall, providing improved access for the operator.

Typically, it is desirable to use the smallest puncture site and smallest equipment that meets the requirements of an intervention. The smaller the puncture site, the easier it is for the entry point to heal without complications and the lower the requirement for closure devices. This can be an enormous cost and morbidity reduction for a particular interventional procedure.

Smaller devices which enable the vasculature to be accessed from the radial artery of the arm (as opposed to the femoral artery in the groin) have enormous advantages from a cost perspective, as the patient is ambulatory immediately after a procedure. Reducing the amount of time a patient has to spend on a gurney or in a bed recovering has additional patient quality of life advantages in addition to the economic advantages of reduced hospital time. Radial artery access requires smaller equipment as has been detailed in the literature extensively. 7 F guides and 6 F sheaths (one French (Fr) equals 0.33 mm) are the largest devices that are recommended for such procedures with the outcomes improving as smaller guides and sheaths are used. Whole Journal issues, Such as *Cardiac Interventions Today* April 2011, Volume 5, No 2, have been dedicated to radial access for procedures and are hereby incorporated by reference. The diameter of the radial artery is such that for 95% of all patients have a radial artery greater than 2.2 mm in diameter and can accommodate a 5 French sheath (typical outer diameter of 6.5 French) or a 6.5 French guide, 60% have a radial artery greater than 2.6 mm in diameter and can accommodate a 6 French sheath (outer diameter 7.5 French) or a 7.5 French guide, 40% have a radial artery greater than 2.95 mm which can accommodate a 7 French sheath (outer diameter 8.5 French) or an 8.5 French guide, and only 20% have a radial artery that is greater than 3.3 mm in diameter which can accommodate an 8 F sheath (outer diameter 9.5 French) or a 9.5 French guide. Saito S et al *Catheter Cardiovas Interve* 1999; 46:173-178. Typically the sheath size irefers to the size of the guide catheter that will fit through it.

A particular difficulty with trans-radial access is providing a guide catheter that can be advanced straight over a guide wire in an atraumatic fashion through the vasculature with a small profile and which can be used to guide a trans-endocardial delivery catheter across small diameter across bends with angles greater than 70 degrees (and preferably 90 degrees or even greater) from the axis of the catheter within the heart while minimizing the potential for damaging the vasculature during advancement to the heart and perforating the heart due to the small diameter of the catheter shaft and the stiffness of the distal region of the catheter.

In some cases, "sheathless" guide catheters can be used without a sheath so that a larger portion of patients may be treated. The use of 5.5 F or 6.5 F sheathless guide catheters can provide a smaller pathway through the radial artery by eliminating the use of a sheath.

Once in the heart, stem cells and other therapeutic substances may be trans-endocardially injected using straight, helical or other injection needles. Helical needles have typically had small bores while the bores of straight needles have frequently been larger. Larger, straight needles have usually been used for delivering large agents such as stem and other cells, cellular aggregates, microspheres, extra cellular matrix (ECM) slurries with effective diameters as large as 80 um and 150 um, particles, and other high viscosity therapeutic agents such as cardiospheres with diameters of 60 to 150 um, and the like. Helical and other small bore needles will typically have difficulty passing such large agents even when the internal diameter is larger than the agents. This is particularly true of aggregated agents which can result in an increase in viscosity that inhibits delivery. While straight, large bore needles are capable of delivering such agents, after injection the stem cells and other large, aggregated substances will often be ejected back into the heart chamber upon contraction of the myocardium, resulting in the loss of the injectable material as well as a risk of embolism in the case of larger agglomerates and particles.

For these reasons, it would be desirable to provide improved systems and methods for the intracardiac delivery of cells, drugs, and other therapeutic agents. It would be particularly desirable to provide improved systems and methods for facilitating introduction of needle-based delivery catheters via a radial artery approach, where such systems preferably include a distal perforation protection system with a minimum space requirement, which is passive and operates without active actuation, and which provides for robust perforation protection capabilities. It would be further desirable to provide improved systems and methods for using needle-based delivery catheters for delivering cells, drugs, and other therapeutic agents with a reduced risk of loss of the injected material back into the heart chamber as a result of heart contraction. At least some of these objectives will be met by the inventions described below.

2. Description of the Background Art. Recently steerable guides and steerable sheaths have been developed that enable significant advantages for trans-endocardial delivery and other cardiovascular procedures. See U.S. Pat. Nos. 7,840,261, 7,402,151, and U.S. Published Application Nos. 2012/0123327 and 2008/0287918, the full disclosures of which are hereby incorporated by reference. Steerable guides and sheaths typically have a wall thickness that is 1 French (One French (Fr) equals 0.33 mm) and standard fixed guides and sheaths typically have a wall thickness of approximately 0.5 Fr.

US Patent Application No. 2012/0123327 (Miller) describes how a 5 Fr or 6 Fr steerable sheath can be used to enter the heart from a radial artery using a guide catheter with a flexible distal end, such as the BioCardia Helical Infusion System. For such a system, a 5 F steerable sheath would have an internal diameter of 5.5 French and an outer diameter of just over 2.2 mm and would easily pass the 5.2 French Helical Infusion Catheter System (BioCardia, Inc.) and operate substantially as a transradial steerable sheath for trasn-endocardial delivery using the Helical Infusion System and would enable a steerable trans-endocardial delivery platform useful in close to 95% of all patients.

Published U.S. Patent Application Nos. 2007/0005018 and 2010/0168713 each discuss the potential advantages of transradial access for trans-endocardial delivery.

Penetration limiter devices on the end of the trans-endocardial delivery catheters are known, such as that described by Eclipse Surgical Technologies in U.S. Pat. No. 6,322,548. These systems are passive systems but consume real estate in the distal end of the catheter and require a distal catheter shaft construction that would prevent transradial access because of size. U.S. Pat. Nos. 7,803,136; 8,361,039; and 8,414,558 also describe distal protection mechanisms for straight needle trans-endocardial delivery systems. These all require an active deployment mechanism which increase the profile of the distal regions and limit the space for advanced therapeutic lumen design such as the inclusion of a contrast port and lumen to discharge at the base of the penetrating element to confirm engagement, to use a large bore helical needle which has importance for the delivery of agents of higher viscosity or which are larger or have a potential to aggregate, and to use a two lumen penetrating element. *Cardiac Interventions Today* April 2011, Volume 5, No 2 and Saito S et al *Catheter Cardiovas Interve* 1999; 46: 173-178 have been described above.

SUMMARY OF THE INVENTION

According to the present invention, methods and systems are provided for intracardiac, trans-endocardial infusion of various materials including drugs, cells, and in particular large cellular aggregations and other particulate substances. Many of the methods and systems are particularly suited for radial artery access but can rely on femoral artery access as well. The systems of the present invention may include multiple interchangeable components such as introducer sheaths, preformed or pre-shaped guide catheters, steerable or deflectable guide catheters, preformed sheathless guide catheters, steerable sheaths or sheath guides, and sheathless steerable sheaths or sheath guides. Each of the variety of guide catheters may be used for the advancement of multiple types of delivery catheters, for example having helical needles, straight needles, coaxial helical needles, coaxial straight needles, double barrel helical needles, double barrel curved needles, double barrel straight needles, large bore straight needles, large bore curved needles, large bore helical needles, and the like. The delivery catheter may also include contrast lumens that discharges at the base of the needle or other penetrating element. These catheter systems may be configured for fluoroscopic navigation, electrical impedance navigation, electromagnetic navigation using real time magnetic resonance imaging, three-dimensional echo navigation, as well as fusion imaging systems that can bring MRI, CT, or echo data and merge it with the fluoroscopic images. Further these delivery systems have potential to enable a broad variety of diagnostic and therapeutic agent delivery some embodiments which will be disclosed as the inventive elements of the delivery system enables these novel therapeutic options.

In a first aspect, the present invention provides methods for introducing needle injection catheters into a heart chamber via a radial artery approach. Such methods comprise advancing a guide catheter through the radial artery (and the intervening arterial vasculature) and into a targeted heart chamber. The catheter will usually enter the right or left ventricle from the right side of the heart but may be further advanced transeptally within the heart to reach the left ventricle from the right side of the heart or other chambers. The guide catheter is positioned to align a distal tip of the guide catheter with a target location on an endocardial wall of the heart chamber. A needle-injection catheter is advanced through a lumen of the guide catheter so that a straight needle projecting coaxially from a distal tip of the needle injection catheter emerges from the distal tip and penetrates the endocardial wall to position an injection port at the tip of the needle in the myocardium. A plurality of penetration limiting elements remain constrained within the guide catheter until the straight needle emerges from the distal tip at which point the elements self-deploy radially outwardly from a base of the needle, typically resiliently deploying as a result of their own spring-force upon the release of constraint, to limit the penetration of the needle into the myocardium in order to reduce the risk of perforation of the endocardial wall.

In exemplary embodiments, positioning may comprise rotating and/or axially translating a guide catheter having a pre-shaped deflection at its distal end. In alternative exemplary embodiments, positioning may comprise deflecting or "steering" the distal tip of the guide catheter while the guide catheter is in the heart chamber. In all cases, the guide catheter will usually be introduced over a guidewire which has been previously placed from the radial artery to the heart chamber in a conventional manner.

In further exemplary embodiments, advancing the needle-injection catheter may comprise constraining the penetration limiting elements in an introduce sleeve. A distal end of the sleeve is engaged against a proximal hub of the guide catheter, and a distal end of the needle-injection catheter is advanced into a proximal portion of the guide catheter while the penetration limiting elements remain constrained.

In still further exemplary embodiments, the penetration limiting elements may comprise resilient petals which have bases attached to the catheter body at the base of the straight needle. The petals may be shaped to curve outwardly from the catheter body when unconstrained. The petals may wire loops folded in a continuous length of a shape memory wire, and a platinum wire may be wound over the shape memory wire to provide radiopacity. Alternatively, the petals may comprise solid leaves or other structures which overlap when folded inwardly against the needle shaft. Typically, in all such embodiments, the catheter includes from two to six petals, most typically being three.

In a second aspect, the present invention provides a needle-injection catheter comprising a catheter body having a distal end, a proximal end, a stiff proximal portion, a flexible distal portion, and a delivery lumen extending therethrough. By stiff, it is meant that the proximal portion of the catheter body will have sufficient column strength and pushability to be advanced through relatively non-tortuous regions of the vasculature and in particular from the radial artery to the heart. By flexible, it is meant that the distal portion will be able to be advanced across small radius curves to allow positioning within the heart chamber and through pre-shaped or deflected regions of the guide catheter. The catheter further includes a straight injection needle extending coaxially from a distal tip of the flexible portion of the catheter body. A plurality of penetration limiting elements are positioned circumferentially about a base of the straight injection needle and are configured to fold radially inwardly against a shaft of the needle when constrained in a tubular lumen and to extend radially outwardly when unconstrained.

The penetration limiting elements of the needle-injection catheters may comprise resilient petals which have bases attached to the catheter body at the base of the straight needle. The petals may be shaped to curve outwardly from the catheter body when unconstrained. The petals may be wire loops folded in a continuous length of a shape memory wire, and a platinum wire may be wound over the shape memory wire to provide radiopacity. Alternatively, the petals may comprise solid leaves or other structures which overlap when folded inwardly against the needle shaft. Typically, in all such embodiments, the catheter includes from two to six petals, most typically being three.

In exemplary embodiments, the stiff proximal portions of the catheter bodies of the needle-injection catheters may comprise a braided polymeric tube and the flexible distal portions may comprise a helical metal coil. The catheter body will typically have a first lumen for delivering an injectable composition to the needle and a second lumen for delivery of a contrast agent to the base of the needle. The needle-injection catheters may further comprise a handle or hub (referred to collectively as handles) on the proximal end of the catheter body, where the handle may include valves, luers, and other fillings and components as needed for connection to sources of material to be delivered, contrast agents, guidewires, and the like. The catheter body will preferably be configured to be delivered through a 6.5 Fr or smaller guide catheter.

In further embodiments of the present invention, a catheter system comprises a needle-injection catheter as described above in combination with a guide catheter having a lumen configured to receive the needle-injection catheter and to radially constrain the plurality of penetration limiting elements when the needle-injection catheter is therein. The guide catheter of such a system may have a pre-shaped bend near its distal end so that the guide catheter can be rotated to align the distal end with a target location on an endocardial wall when the guide catheter is in a heart chamber. Alternatively, the guide catheter may have a deflectable (also referred to as steerable) distal end to allow aligning the distal end with a target location on an endocardial wall when the guide catheter is in a heart chamber.

In a third aspect, the present invention provides a large-bore needle injection catheter comprising a catheter body having a distal end, a proximal end, and a delivery lumen extending therethrough. A helical needle extends from the distal end of the catheter body and has at least one helical delivery lumen connected to receive an injectable substance from the delivery lumen of the catheter body. The delivery lumen and the at least one helical lumen are sufficiently large to permit the passage and injection of drugs or biological materials having a mean diameter of at least 100 μm. The catheter body delivery lumen usually has a diameter of at least 0.50 mm, typically being 0.71 mm in its major non circular axis, and the helical lumen usually has a diameter of at least 0.2 mm, typically being about 0.43 mm.

In specific embodiments, the catheter body has at least one lumen in addition to the delivery lumen and the helical needle has at least two helical delivery lumens with one connected to at least the each of the catheter body lumens. The catheter body may comprise a stiff proximal portion and a flexible distal portion, as described above, wherein the stiff proximal portion of the catheter body may comprise a braided polymeric tube and the flexible distal portion of the catheter body may comprise a helical metal coil. The catheter body may include a first lumen and optionally a second for delivery of an injectable composition to the needle and further optionally a second or third second lumen for delivery of a contrast agent to the base of the needle, and a handle may be disposed on the proximal end of the catheter body.

In further embodiments of the present invention, a catheter system comprises a large-bore catheter as described above in combination with a guide catheter having a lumen configured to receive the large-bore catheter. The guide catheter of such a system may have a pre-shaped bend near its distal end so that the guide catheter can be rotated to align the distal end with a target location on an endocardial wall when the guide catheter is in a heart chamber. Alternatively, the guide catheter may have a deflectable (also referred to as steerable) distal end to allow aligning the distal end with a target location on an endocardial wall when the guide catheter is in a heart chamber.

In a fourth aspect of the present invention, a method for delivering a particulate material into an endocardial wall of a heart chamber of a beating heart comprises intravascularly introducing a large bore needle injection catheter having a helical needle into a heart chamber. Particulate materials that may be delivered include cells, stem cells, stem cell aggregates, and any other therapeutic or diagnostic substances which may present a risk of embolism if accidentally released into a heart chamber when injected, particularly as a result of being extruded or otherwise expelled from the injection site as a result of the contraction of the myocardium as the heart beats. The helical needle of the large bore needle injection catheter is advanced into an endocardial wall of the heart chamber so that a port on the needle lies near an interior end of a helical tissue tract formed by the needle. The particulate material, typically having a mean particle diameter of at least 100 μm, is injected through the needle into the interior end of the helical tissue tract. Flow back of the injected material through the helical tissue tract is inhibited in the helical shape of the tract even after the helical needle is withdrawn.

In specific embodiments of the particulate delivery methods, the catheter will have a catheter body with a delivery lumen having a diameter of at least 0.50 mm, preferably being in the range from 0.50 mm to 0.80 mm. The helical needle will usually have a helical lumen with a diameter of at least 0.2 mm, preferably being in the range from 0.21 mm to 0.56 mm. The catheter body delivery lumen usually has a diameter of at least 0.50 mm, typically being 0.71 mm in its major non circular axis, and the helical lumen usually has a diameter of at least 0.2 mm, typically being about 0.43 mm. The catheter body typically has at least one lumen in addition to the delivery lumen, and the helical needle typically has at least two helical delivery lumens with one connected to at least the each of the catheter body lumens.

BRIEF DESCRIPTION OF THE DRAWINGS

FIGS. 8A-1 through 8F-6 illustrate design and fabrication detail of a needle-injection catheter having a straight injection needle surrounded at its base by penetration limiting elements according to the present invention.

In this patent application we will disclose inventive elements of each of these, but their usage is in no way limited to the other elements in this application.

DESCRIPTION OF THE INVENTION

Figure 1:
FIGS. 1 and 2 illustrate prior art guide and delivery catheters that may be used in certain implementations of the present invention.

FIG. 1 (Prior Art) shows a preformed 6 F Hockey Stick (HS) 90 cm guide catheter 100, such as the ConcierGE® Guiding Catheter, available from Merit Medical Systems, Inc., which is advanced straight or over either a dilator or a guide wire from either the femoral or radial artery. Because the distal segment is highly flexible, the guide catheter may be safely advanced across the aortic valve into the left ventricle. The guide catheter 100 may be advanced into a femoral artery using any commercially available 6 Fr sheath. For radial access, a longer 25 cm sheath such as the Boston Scientific Super Sheath Catalog 16037-06B is preferred to avoid complications with radial artery spasm which occurs frequently in patients.

Figure 2:
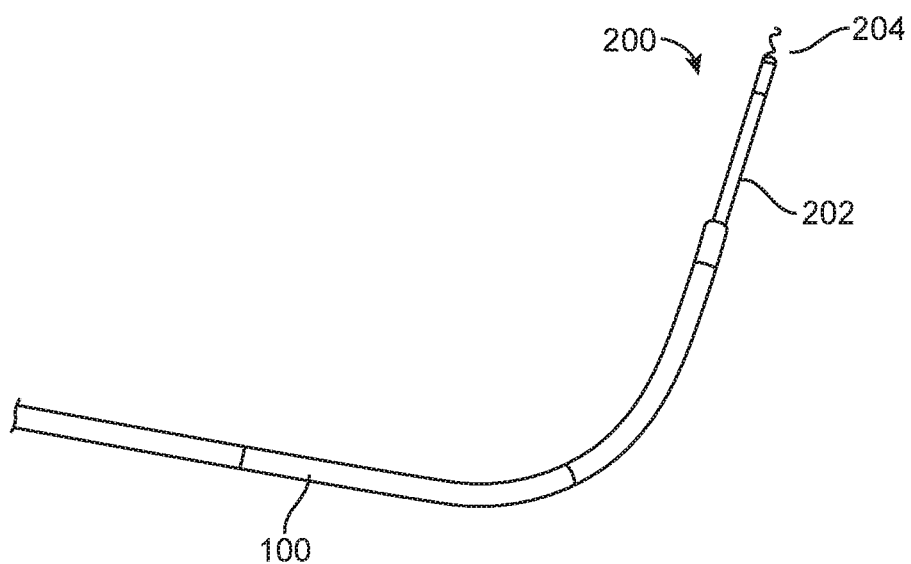

FIG. 2 (Prior Art) shows the preformed 6 Fr HS 90 cm guide catheter 100 after a central straightening element, such as a dilator or wire, is removed and a trans-endocardial infusion catheter 200 with a highly flexible distal segment 202 with a length of at least 6 to 10 cm which reaches beyond the end of the guide catheter between 3.5 cm and 7 cm is inserted. Here the penetrating element is a helical needle 204 which may readily be rotated within the fixed guide and advanced in order to engage the catheter into the heart tissue. The highly flexible distal segment 202 on the trans-endocardial infusion catheter 200 does not straighten the highly flexible guide portion on the 6 Fr guide catheter enabling one to advance and rotate the fixed guide and then extend the helical needle 204 to the ventricular wall with the trans-endocardial delivery system to penetrate tissue and accomplish therapeutic or diagnostic delivery. The preformed guide shape will typically bend at least 90 degrees as there will be some slight straightening as the trans-endocardial infusion catheter is inserted due to the need for the guide distal end to be flexible. In FIG. 2, the trans-endocardial infusion catheter 200 is a BioCardia® helical needle model 953L catheter where the highly flexible region comprises a multifilar coil design but other flexible segments can be used in the present invention, e.g. the flexible segment could be made from an etched stainless steel tube such as shown in U.S. Pat. Nos. 5,228,441; 5,243,167; 5,322,064; 5,329,923; 5,334,145; 5,454,787; 5,477,856; and 5,685,868, or form a wound ribbon structure. The bending rigidity of such coil designs can be readily calculated by following validated closed form derivations for such complex geometries, as taught for example in Meagher, J., Altman, P.: Stresses from Flexure in Composite Helical Implantable Leads, Medical Engineering and Physics, Vol. 19, No. 7, pp 668-673, 1997.

Penetrating elements in different aspects of the present invention can be straight needles, curved needles, multi-pronged needles, and the like, as well being helical needles. As the pre-shaped catheter guide catheters used in the methods and systems of the present invention may be axially advanced and retracted and rotated in the left ventricle, a static sheath will typically be placed in the first 25 cm of the radial artery to reduce the impact of radial artery spasm on the procedure as well as the viability of the radial artery at the end of this procedure. A long 6 F sheath may also be used with a 6 Fr guide to minimize the potential for a spasm to bind the inserted catheter and prevent completion of the procedure.

In some embodiments, a 25 cm 6 Fr introducer sheath and a 110 cm preformed 6 Fr guide catheter with a preformed 100 degree hockey stick angle are used to advance a 5.2 Fr trans-endocardial delivery catheter with a penetrating element mounted on the end of a highly flexible coil. These catheters may have two lumens which travel to the distal end, one of which discharges at the base of the penetrating element and one which passes through the penetrating element to discharge into the tissue penetrated. Further, this catheter system in its preferred embodiment has a helical needle at its distal tip, eliminating the need for perforation protection device. Clearly, eliminating the need for the 25 m 6 Fr sheath by providing a lubricious coating and enabling the 110 cm guide to be used as a sheathless guide enables the system to be used in an additional 35% of the population, and is the preferred embodiment for patients with smaller radial arteries.

Alternative systems may utilize a steerable 6 Fr guide catheter with an outer diameter set to accommodate the 6 Fr sheath (6.4 Fr or smaller) and an inner diameter selected to accommodate a 4 Fr infusion catheter with an internal diameter of 3.9 Fr to 4.4 Fr. Such steerable guide catheters are commercially available, and a suitable steerable guide catheter is the Universal Deflectable Guide Catheter model #1066, manufactured by BioCardia, Inc., which has a 4.25 Fr internal lumen and a 6 French outer lumen. This approach has the same procedural advantages as the first embodiment disclosed here, but also benefits from the ability to deflect the distal end of the guide providing enhanced control options and also the ability to have greater back up support within the ventricle. This system may also be used with a 25 cm radial access sheath, but it is challenged by the ability to pass a larger diameter helical needle and thus a straight needle system with a passive perforation protection system is desired which will be described.

An alternative steerable guide catheter suitable in certain embodiments of the present invention is disclosed in US Patent Publication No. 2012/0123327, the full disclosure of which is incorporated herein by reference. This guide catheter allows entry with a 5 French steerable sheath (outer diameter 7.5 French) without an introducer sheath. Although there is added risk of radial artery spasm associated with the manipulation of the device within the artery, its steerable nature may significantly reduce the manipulations relative to that of a 6 Fr sheathless fixed guide which has a 7 Fr outer diameter. Both this sheathless guide and this steerable sheath system would benefit from a lubricious coating along the full length of the catheter shaft. The potential to use larger steerable sheaths for the procedure to accommodate larger catheters for trans-endocardial delivery which have different fluid delivery, electrical mapping, ultrasound sensing, electromagnetic positioning, and other such well understood geometric requirements may be performed with the caveat that the larger the catheter the more risk to the radial artery may result. Currently, tri-lumen fluid management with bipolar sensing, as disclosed in U.S. Pat. No. 7,736,346, has been realized in a 5.2 Fr envelope which is 5 Fr sheath compatible.

Figure 3A:
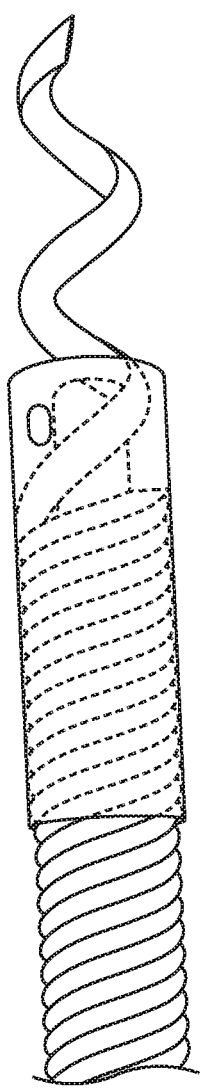
FIGS. 3A and 3B illustrate helical delivery catheter implementations of the present invention.
Figure 3B:
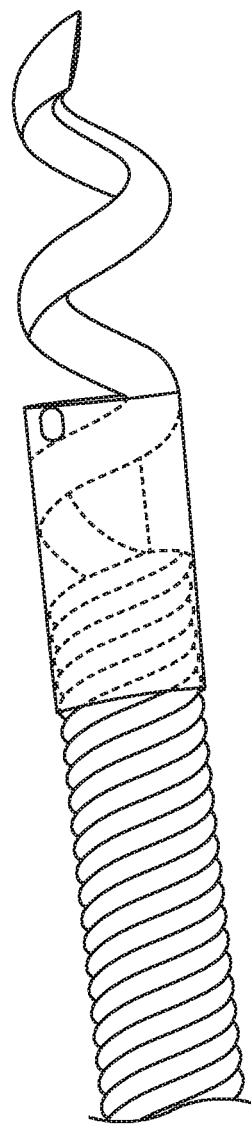

FIGS. 3A and 3B shows the distal end of two trans-endocardial delivery catheters, each having two lumens: one lumen which is used for the delivery of contrast media and terminates at the base of the helical needle and one which goes all the way to the distal end of the helical needle. These needles are formed with a winding fixture that controls pitch and which has channel width specified to prevent flattening or excess "ovalization" (an unintended deformation of the cross-section from a circular geometry to an oval or similar non-circular geometry) of the circular needle cross-section. Needles are made from 304 stainless steel although other materials can also work. In attaching the helical needles to the distal end of the catheter the needles are bonded into the dual lumen internal tubing that is covered with the distal multifilar coil, a mandrel is inserted into the contrast discharge lumen to protect its patency, and the helix is embedded in an epoxy resin, such as Loctite M-31CL where the needle is firmly secured to the distal highly flexible coil. The smaller diameter helical needle has an internal diameter of 0.008 inches and the larger diameter Helix has an internal diameter of 0.022 inches.

Figure 4A:
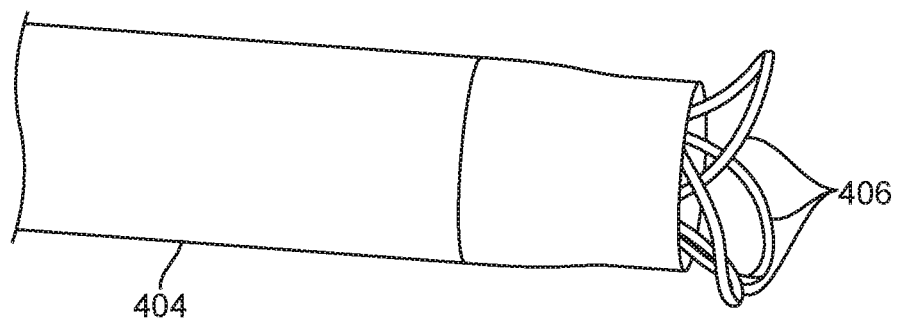
FIGS. 4A and 4B illustrate a needle-injection catheter having a straight injection needle surrounded at its base by penetration limiting elements according to the present invention being advanced from a guide catheter.
Figure 4B:
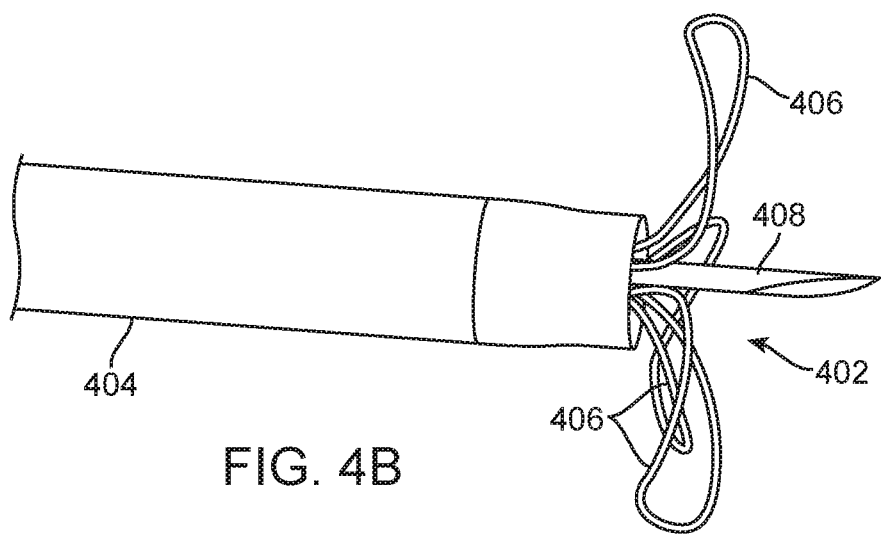

FIGS. 4A and 4B show the distal end of a straight needle trans-endocardial catheter 402 system including a delivery catheter 404 that has a passive perforation protection system comprising a plurality (three) protective petals 406 surrounding the base of a straight injection needle 408. FIG. 4A shows the system as it is being deployed, and FIG. 4B shows it as it fully deployed. The systems of the present invention includes the catheter of the present invention in combination with a guide catheter which could be anyone of a variety of conventional steerable or fixed guide catheters having a 5.2 Fr lumen or, in some cases a 4 Fr lumen. The system may optionally further include an introducer sleeve 817c, as shown FIG. 8E, that may be a thin-walled slit tube of roughly three to ten centimeters in length that is advanced over the proximal shaft of the needle injection catheter to retract perforation protection device within a lumen of the sleeve. The catheter can then be advanced from the introducer sleeve into the guide catheter which will be used to deliver catheter after the introducer sleeve is removed.

Figure 5:
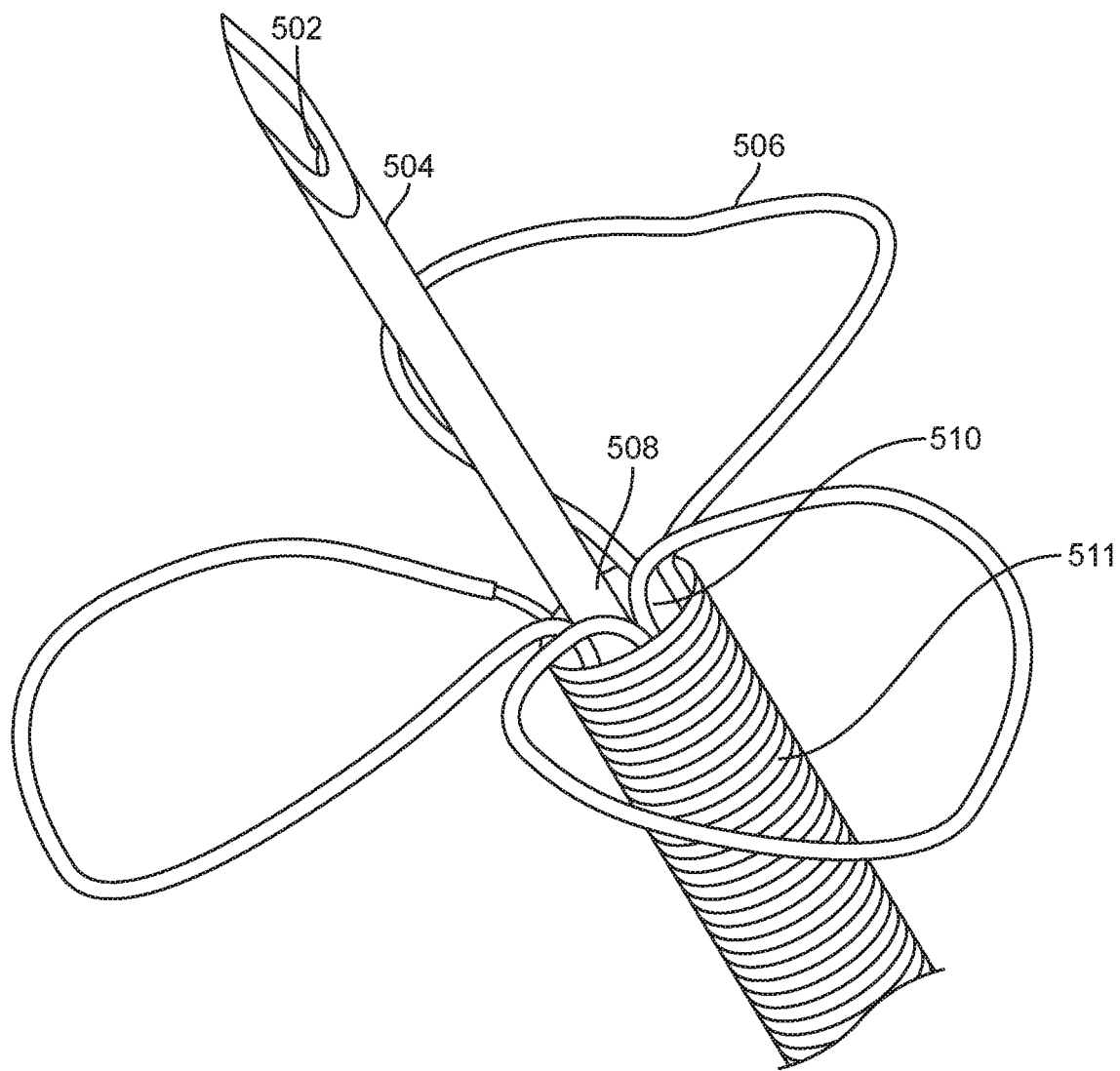
FIG. 5 illustrates the distal tip of a needle-injection catheter having a straight injection needle according to the present invention.

FIG. 5 shows the distal end of a trans-endocardial delivery system that is compatible with a 5.5 Fr lumen catheter introducer system 500 in which a straight needle 504 is mounted on the distal end of a flexible distal region 511 of a catheter body or shaft. A contrast port 510 is disposed at a base of petals 506 which are attached at a distal end of the region 511. The straight needle 504 may be a 27 Gage regular wall needle with a 0.008" inch lumen, and a 0.016" outer diameter and an exposed length of 0.160, 0.240, or 0.320. Tip 502 of needle 504 preferably has three facets, as shown, but could alternatively have one or two facets The penetration-limiting petals 506 may be formed from Nitinol® wire 0.0035 inches in diameter which has been served or covered with a coil of single filar 0.0015" diameter platinum iridium (Pt/Ir) 90/10) wire over the top for radiopacity. The flexible region of the catheter may be formed from five filar 0.008" wire coil 511 with an outer diameter of 0.063" with a pitch of 0.046" which extends ten centimeters from the more rigid catheter shaft. A dual lumen PEBAX 55D polymer tubing (not shown in FIG. 5) typically extends most or all of the length of the catheter. The base of the straight needle penetrating element 508 is inserted into and bonded to one of two lumens of the dual lumen tube. The stem or base of the penetration limiting/perforation protection structure is inserted 510 into the pentafilar coil 511 but will typically leave one of the internal lumens open to discharge a contrast medium when needed.

The penetration limiting/perforation protection device can be implemented in a number of ways. In a preferred embodiment, a monolithic structure includes a plurality of petals which are partially or completely covered with the Pt/Ir wire coil. The wire covering facilitates assembly and improves longitudinal and radial spacing consistency. The covering may also enhance security of attachment. Assembly is performed by straightening the superelastic wire (which is preformed or set to have the three dimensional petal geometry illustrated herein), and the Pt/Ir coil is advanced over the straightened wire. The petal wire is then allowed to resume its relaxed multi-petal shape, and the penetration limiting/peroration protection structure is bonded with epoxy into the distal end of the catheter body or shaft as noted previously. Additionally or alternatively, the penetration limiting/perforation protection structure may also be attached using braze, solder, or by welding to the needle and/or the distal coil.

Other embodiments include the use of distinct parts for each petal in a plurality of petals. Combinations of these are also possible, i.e. two petals in one monolithic structure and two petals in another monolithic structure, resulting in a four petal configuration, etc. Further more limited embodiments in which only one petal deploys from the catheter on one side.

The number of petals or leaflets is significant as it determines the number of individual wires that must anchored. Fewer leaflets thus occupy less of the available space inside the catheter but can result in thicker elements. Since bending stiffness tends to be a third order factor on diameter, doubling the diameter gives 8 times the stiffness. Thus anticipated that three loops allows more stiffness (thus resistance to puncture) than four, and perhaps more stable a geometry than two loops. The preferred embodiment has three loops but this should not limit the invention disclosed. The Nitinol® wire can also be selected from a range of sizes, typically 0.002 to 0.005 inches in diameter.

Apparent Cross Sectional Area Relates to Puncture Resistance: In the context of perforation protection, the element of interest is the distal end of the main catheter body and not the "penetrating element" or needle. The force required to cause myocardial perforation/puncture is related to the presented cross sectional area of the tip of the catheter. The wire loop elements disclosed in this application effectively increase the apparent surface area of the distal end of the catheter body, thus increasing the force which would be required to cause myocardial perforation.

Figure 6A:
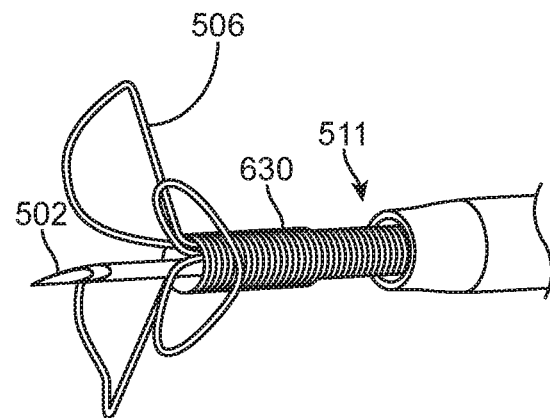
FIGS. 6A through 6E illustrate retraction of a needle-injection catheter having a straight injection needle surrounded at its base by penetration limiting elements into a guide catheter according to the present invention.
Figure 6B:
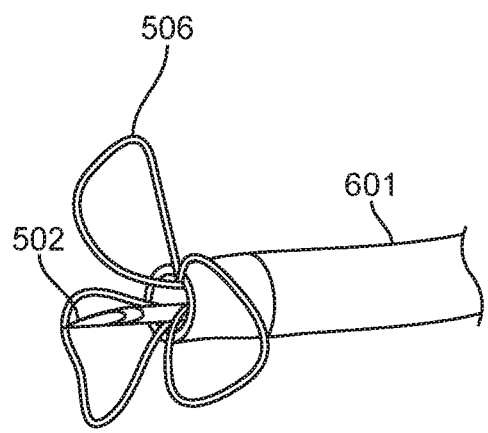
Figure 6C:
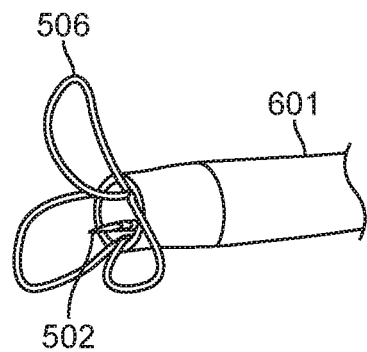
Figure 6D:
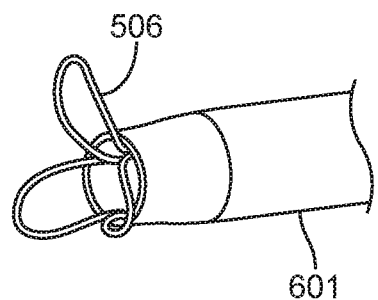
Figure 6E:
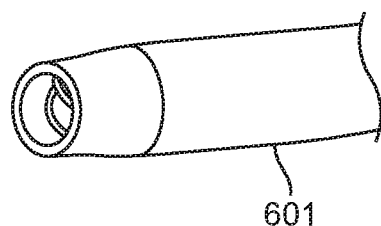

Variable stiffness of the loops: Since the root of each loop or petal near the distal end of the catheter body is the portion of the loop/petal which is the most resistant to being bent backwards (shortest lever arm to cause the bending), it is the most important to creating puncture resistance, and could be made stiffer than the portions of the loop further from the catheter tip, making the system more atraumatic, or more sensitive to contact with fine structures within the heart. FIG. 6A through 6E show exemplary loop/petal structures which are suitable as the penetration limiting/perforation protection elements of the present invention and which readily collapses when deployed from or retracted into the distal end of a guide catheter. FIGS. 6A through 6E specifically show the penetration limiting/perforation protection system as the delivery catheter is being retracted back into the guide catheter: FIG. 6A shows the distal region 511 of the infusion catheter extended from a guide catheter 601 with protective petals or leaflets 506 at full deployment. FIG. 6B shows the leaflets or petals 506 fully deployed just before entering the guide catheter 601 as the delivery catheter is retracted into the guide catheter 601, FIG. 6C shows the leaflets or petals 506 starting to collapse around the needle 502 and into the guide catheter 601, FIG. 6D show the leaflets or petals 506 just prior to full capture by the guide catheter 601. FIG. 6E shows the perforation protection system completely retracted and barely visible through the distal port of the guide catheter 601. This final position is referred to as the "garaged" state, when the delivery catheter is protected within the guide and the guide can be manipulated to target specific region within the ventricle. This protection device more than doubles the force to penetrate the heart tissue with a given 5 French straight needle catheter system. "Flower petals" passively expand/collapse when extended out from/drawn in to catheter, and when collapsed, the tips of the loops extend past the tip of a straight needle to inhibit gouging the ID of catheter, or tissue when partially retracted. In its deployed configuration, the penetration limiting/perforation protection system significantly reduces the risk of perforation with a straight needle system.

Figure 7:
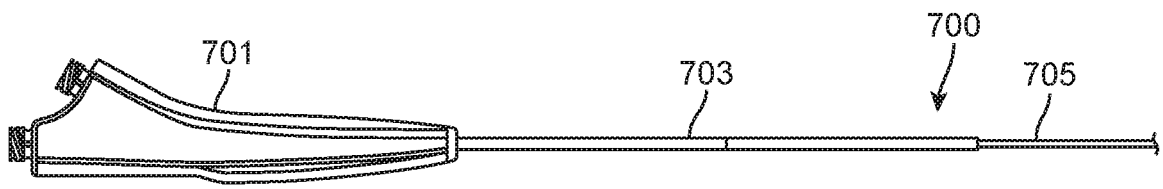
FIG. 7 illustrates an exemplary delivery catheter having two lumens and a handle assembly.

A proximal portion 700 of a delivery catheter with two fluid lumens is shown in FIG. 7 and includes a handle assembly 701 attached to a main catheter shaft 705 by a strain relief assembly 703. The catheter shaft 705 is a flexible, torquable composite conduit for the therapy and contrast delivery lumens. The strain relief assembly 703 serves as a protective transition between the catheter shaft and the handle assembly 701. Although the helical needle systems of the present invention may have a lower likelihood of perforation than the straight needle embodiments, there may be advantages to including such a perforation protection embodiment to a helical needle catheter which can be readily implemented.

Figures 1, 8A:
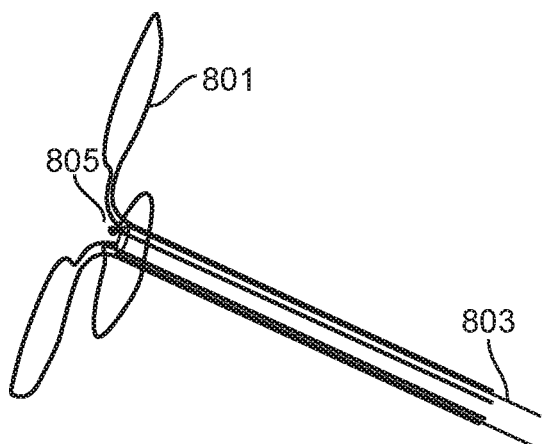
Figures 2, 8A:
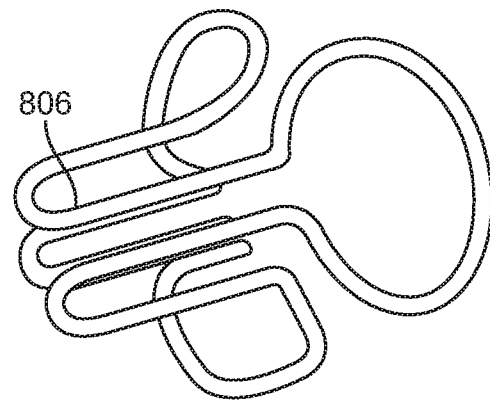
Figures 3, 8A:
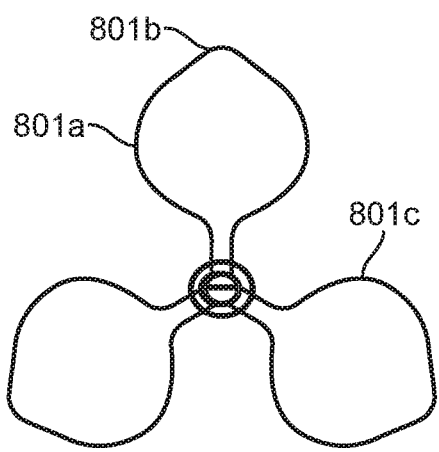
Figures 4, 8A:
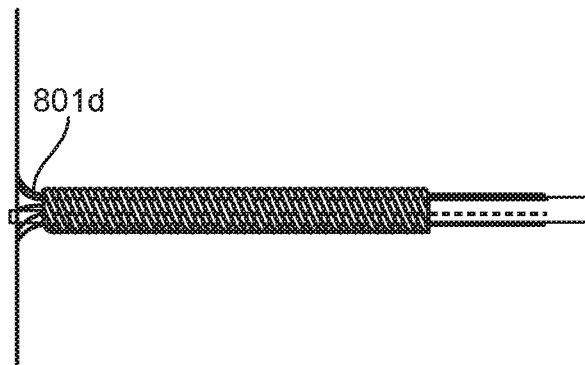
Figures 1, 8B:
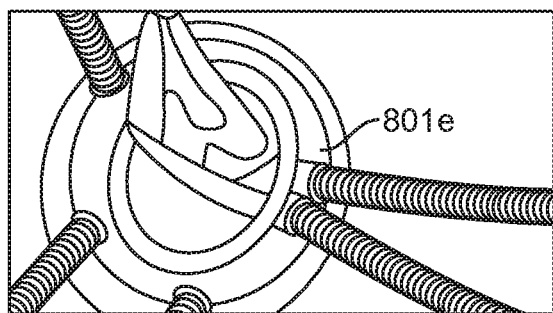
Figures 2, 8B:
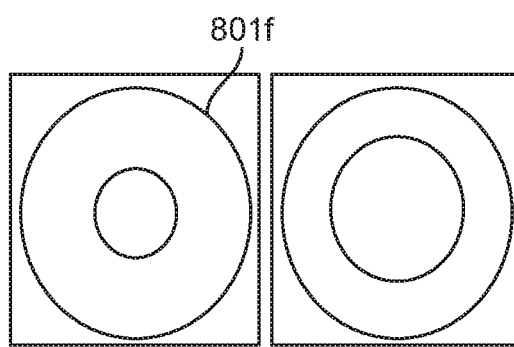
Figures 3, 8B:
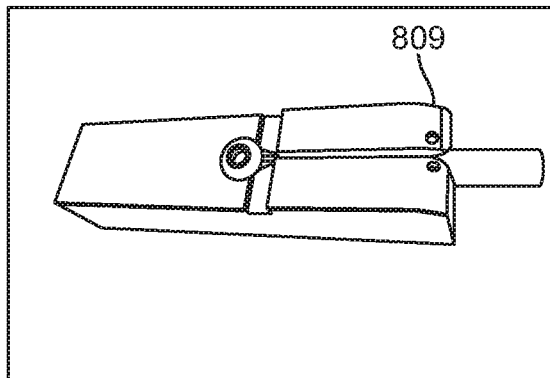
Figures 4, 8B:
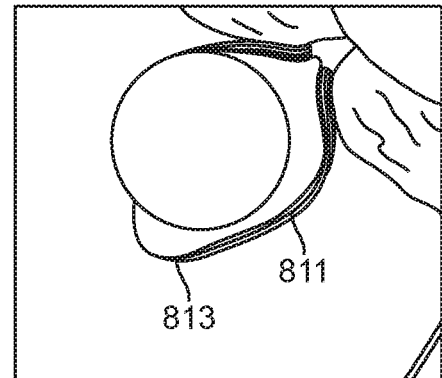

FIG. 8A (panels 1-4) illustrates a penetration limiting/peroration protection including exemplary leaflet or petal elements. The leaflet elements 801 can be independent as shown above, or can have connected legs in what we would call a "monolithic structure" 806, e.g. all leaflets or petals may be formed from a single length of Nitinol® or other shape memory metal or polymer, where the length is further optionally connected at the ends to form a continuous structure with multiple loops. The legs can be of straight or have some other convoluted shape to improve bonding in an adhesive junction. The loops have several radii which aid in the collapse and/or expansion of the structure during sheathing and deployment. A major diameter 801*a* primarily defines the sheathed length relative to the needle which is covered and protected. The "folding blip" 801*b* is designed to prevent plastic strain upon sheathing where that segment of geometry is folded 180 degrees. The "root" radii 801*d* make sheathing easier, as the lever arm for folding down the leaflet is increased when this radius is increased. Radiopacity can be provided by covering the leaflets with coiled platinum 801*e* as shown in FIG. 8B (panel 1), or made from drawn filled tube (DFT) with a radiopaque center such as platinum 801*f* as shown FIG. 8B (panel 2). Radiopacity coils can be attached with geometric binding, solder, or glue Panel 3 and 4 of FIG. 8B show the loops are made by heat setting on a mandrel which has features to create the various chosen radii for example 809, 811, and 813.

Figures 1, 8C:
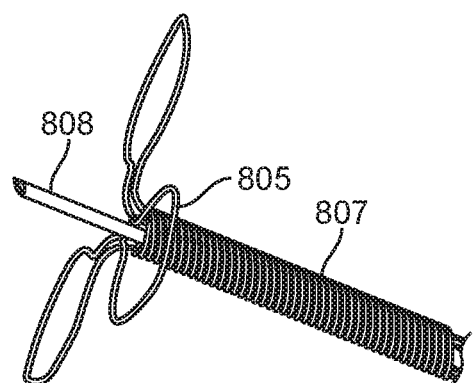
Figures 2, 8C:
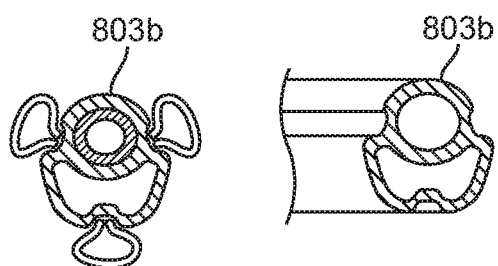
Figures 3, 8C:
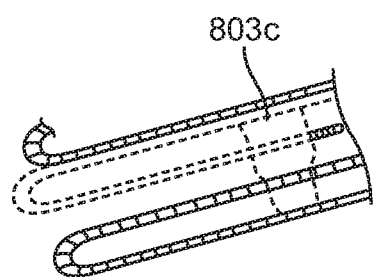
Figures 4, 8C:
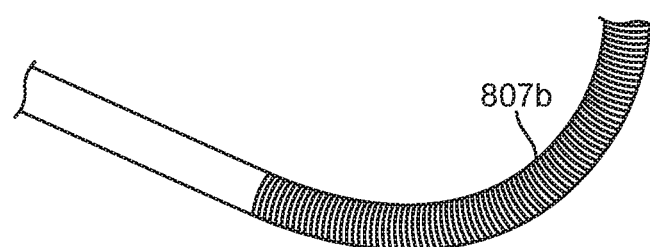

FIG. 8C shows the dual lumen tube. The dual lumen 803*b* (panel 2) has a channel for therapeutic and a channel for contrast. The therapeutic path is connected to the injection element 808 and delivers agents into the tissue. The contrast lumen opens at the tip of the shaft 805, and contrast is injected through it to assure correct positioning against the tissue surface. Options for the dual lumen include a non-round extrusion 803*b* with recesses for the legs of the leaflets optimizing cross sectional flow area, or a round extrusion could be blow molded to fit around the legs of the leaflets 803*c* (panel 3), again optimizing flow area, and also potentially improving leaflet security in bonding to the shaft. Tissue engagement indicators can provide additional feature/benefit of a radiopaque loop is the possibility of having it act as a tissue engagement indicator. Since the tips of the wire loops may be shaped as to "lead" the tip of the catheter by some distance, as the needle punctures the tissue and the distal end of the body of the catheter approaches the tissue surface, the tips of the loops bending back can be visualized under fluoroscopy. A potential added benefit of using the loops to indicate tissue engagement is the possibility of being able to eliminate the contrast lumen from the shaft, which could enable overall system size reduction or accommodate larger therapeutic lumens which enable the delivery of larger cells, cell aggregates, microspheres, Extra Cellular Matrix (ECM) slurries, particles, or higher viscosity therapeutic agents. The loops could be configured such that they form a generally conical shape, a flared bell shape like a trumpet, or closing bell shape like a toilet plunger.

Figure 8D:
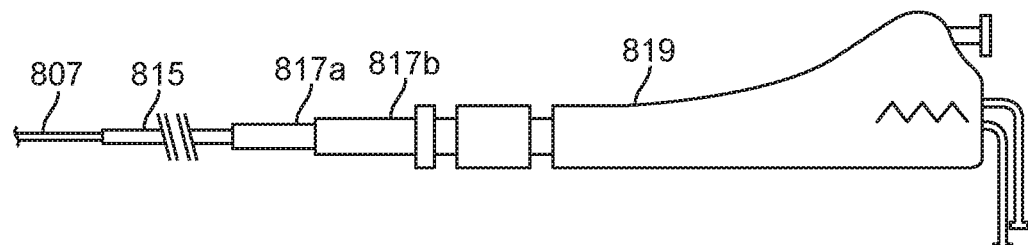
Figures 1, 8E:
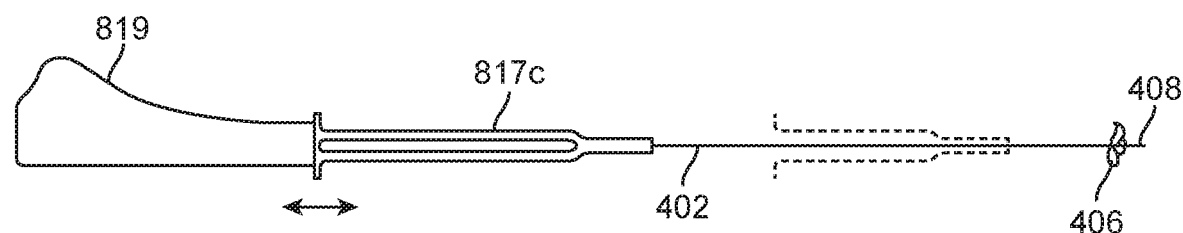
Figures 2, 8E:
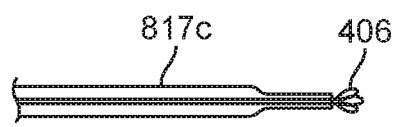
Figures 3, 8E:
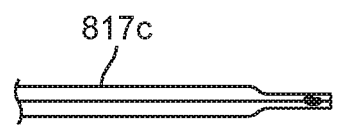

FIG. 8D shows the distal flexible element and needle. The pentafilar coil 807 is a five element coil of 0.008" wire with a pitch of 0.046". This flexible element could optionally be comprised of a cut metal tube 807b (FIG. 8C), which may have the advantages of thinner wall, and variable flexibility along its length, which if stiffer at the more proximal region, could improve column support thus improving ability to penetrate tough tissue at long extensions out of the steering delivery guiding catheter. The shaft typically comprises three main including the highly flexible distal segment 807, the main length of the shaft 815 and the strain relief segment 817. Note, the following items are also referenced in FIG. 7 as the main shaft, 705, and strain relief, 703.

The flexible element is as previously mentioned, may be fabricated of a five filar coil of stainless steel round wire 807. The main shaft is comprised of the outer jacket (braided polyamide) 815, and the inner dual lumen (Pebax) 803 (FIG. 8A). The strain relief 817 contains an extension of the main shaft and dual lumen 815 and also has two segments of PEEK, one smaller 817a which fits inside the handle of the guiding catheter, and one larger 817b which can enter a rotating hemostasis valve (RHV) attached to the proximal luer of the guide catheter, but which does not enter the handle of the guide. The step at the end of the larger OD between the two strain relief sections is used as a reference point touched by the user to assess that the distal tip is just "garaged" within the guiding catheter while that junction is just at the proximal edge of the RHV.

Optionally, an introducer sheath can be slidably attached to the handle, shaft along the shaft, and cause the leaflets to fold forward for introduction into the guiding catheter. This element can become part of the strain relief, e.g. a snap fit design 817c (panel 1, FIG. 8E). The junction between the main shaft segment 815 and the distal flexible element 807 is formed with a thin walled hypotube or "bushing" bonded in place with cyanoacrylate adhesive. The junctions from the main shaft 815 to the strain relief 817 and the strain relief to the handle 819 may be made by epoxy adhesive, reference FIG. 8D.

Wire assemblies, e.g. 801 and 806 of FIG. 8A, may be pre-tinned with Au—Sn solder, then soldered to a stainless steel needle & coil (or other flexible spring element) as a subassembly for simplification of manufacture. The radius of curvature of the wire as it leaves its attachment point should not be smaller than 10 times the wire diameter. Smallest recommended ratio is approximately 5.6:1, but that will likely plastically deform with use and have reduced fatigue life. Monolithic set of wire loops provide for ease of assembly, for consistency of longitudinal and radial spacing, and for increased security in attachment as opposed to single individual leaflets with straight "legs").

FIG. 8D shows the distal flexible element and needle in including a pentafiler coil 807 which is a five element coil of 0.008" wire with a pitch of 0.046". This flexible element could optionally be comprised of a cut metal tube 807b (FIG. 8C), which may have the advantages of thinner wall, and variable flexibility along its length, which if stiffer at the more proximal region, could improve column support thus improving ability to penetrate tough tissue at long extensions out of the steering delivery guiding catheter. The shaft 807, 815, and 817 includes three main segments (FIG. 8D): the highly flexible distal segment 807, the main length of the shaft 815, and the strain relief segment 817.

The therapeutic lumen and contrast lumen will typically run uninterrupted the full length of catheter shaft. A junction between the pentafiler coil 807 and the polyamide jacket 815 is formed with an adhesive lap joint. This has been formed by Loctite 4014 bonding to either a thin walled 304 stainless bushing, not shown, with an ID/OD 0.038"/0.042"×0.3" long, or using the outer surface of the lumen assembly as the lap joint material. Proximal to the coil-shaft junction, the main shaft outer jacket is a flexible torquable composite comprised of an 0.042" ID by 0.054" OD polyamide tube with 0.0015" wire braid (16 carrier) encapsulated in the wall 815.

The strain relief assembly 703 serves as a protective transition between the catheter shaft and the handle assembly 701. As shown in FIG. 8D, the strain relief 81 contains an extension of the main shaft and dual lumen 815 and also has two segments of PEEK, one smaller (0.062" ID×0.010" wall) 817a which fits inside the handle of the guiding catheter, and one larger (0.085" ID×0.010" wall) 817b which can enter a rotating hemostasis valve (RHV) 1902 attached to the proximal luer of the guide catheter 1901, but which does not enter the handle of the guide. The step between the two OD's can be used as a reference point, touched by the user to assess that the distal tip is just "garaged" within the guiding catheter while that junction is just at the proximal edge of the RHV without having to expose the patient to increased radiation by using fluoroscopy to verify needle tip position.

Figures 1, 8F:
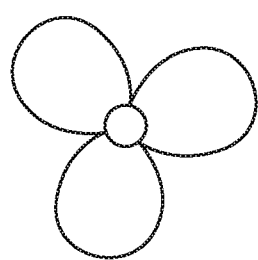
Figures 2, 8F:
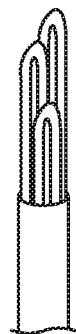
Figures 3, 8F:
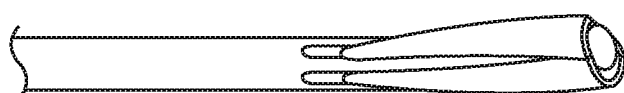
Figures 4, 8F:
Figures 5, 8F:
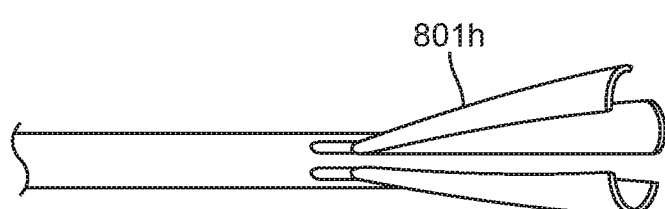
Figures 6, 8F:
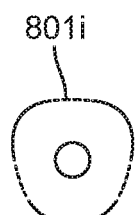

FIG. 8F, panels 1 and 2, shows that in cases where packing may be slightly too tight, the loops at the tip take up more space than the main body of the loop, so the tip positioning (in collapsed state) may be staggered axially (panel 2) either by staggering the root position, or by having differing loop sizes. The leaflets may be made so that they are self-reinforcing in a deployed configuration to reduce ease of fold back. One approach is for each loop threaded through an adjacent loop as shown. Another variation shown is a "steam colander" variation 801h (panels 3-6), with flexible sheets, or plates in curved triangular segments of conical section. Optionally the edges can have a folding or sliding interlocking mechanism to limit "splay" 801i.

Figure 9:
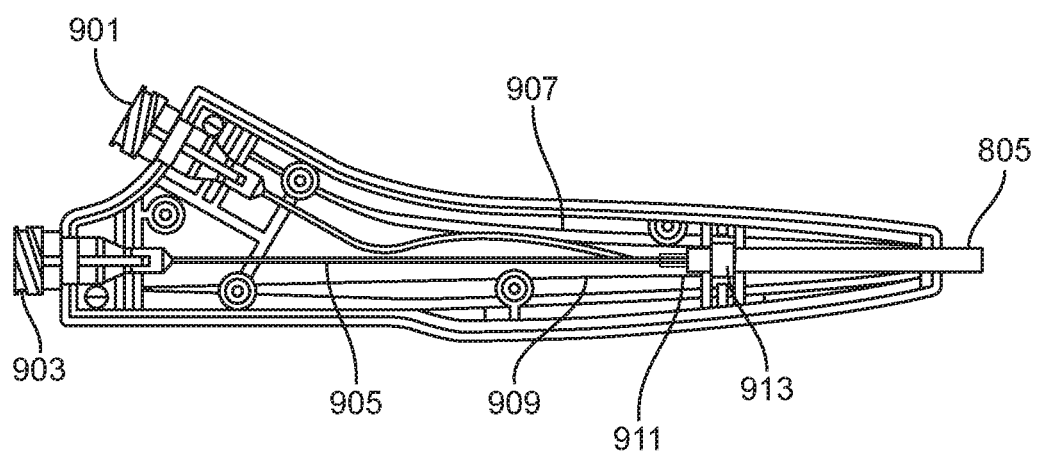
FIG. 9 is a cross sectional view of a handle assembly for a needle-injection catheter according to the present invention.

FIG. 9 is a cross sectional view of the handle assembly 701 from FIG. 7 which can be standard for many of the dual lumen catheters here. The handle is an ergonomic catheter control feature containing the proximal ports of both the therapy and contrast lumens 901, 903. The catheter shaft 805 is secured directly to the strain relief assembly using epoxy adhesive such as Loctite M-06FL. A retaining block 913 is used to integrate the strain relief assembly and catheter shaft with the handle assembly using Loctite 4013 cyanoacrylate adhesive. Inside the handle assembly the catheter shaft 911 terminates just proximal to the retaining block.

At the main shaft termination, the contrast lumen 907 is isolated and directed toward the contrast proximal luer 901. At the catheter shaft termination, 911, the therapy lumen is also isolated and a bushing, 909, is used to connect an extension tube, 905, to the therapy lumen in the main shaft. The proximal end of the extension tube is connected to the therapy proximal luer, 903.

Figure 22:
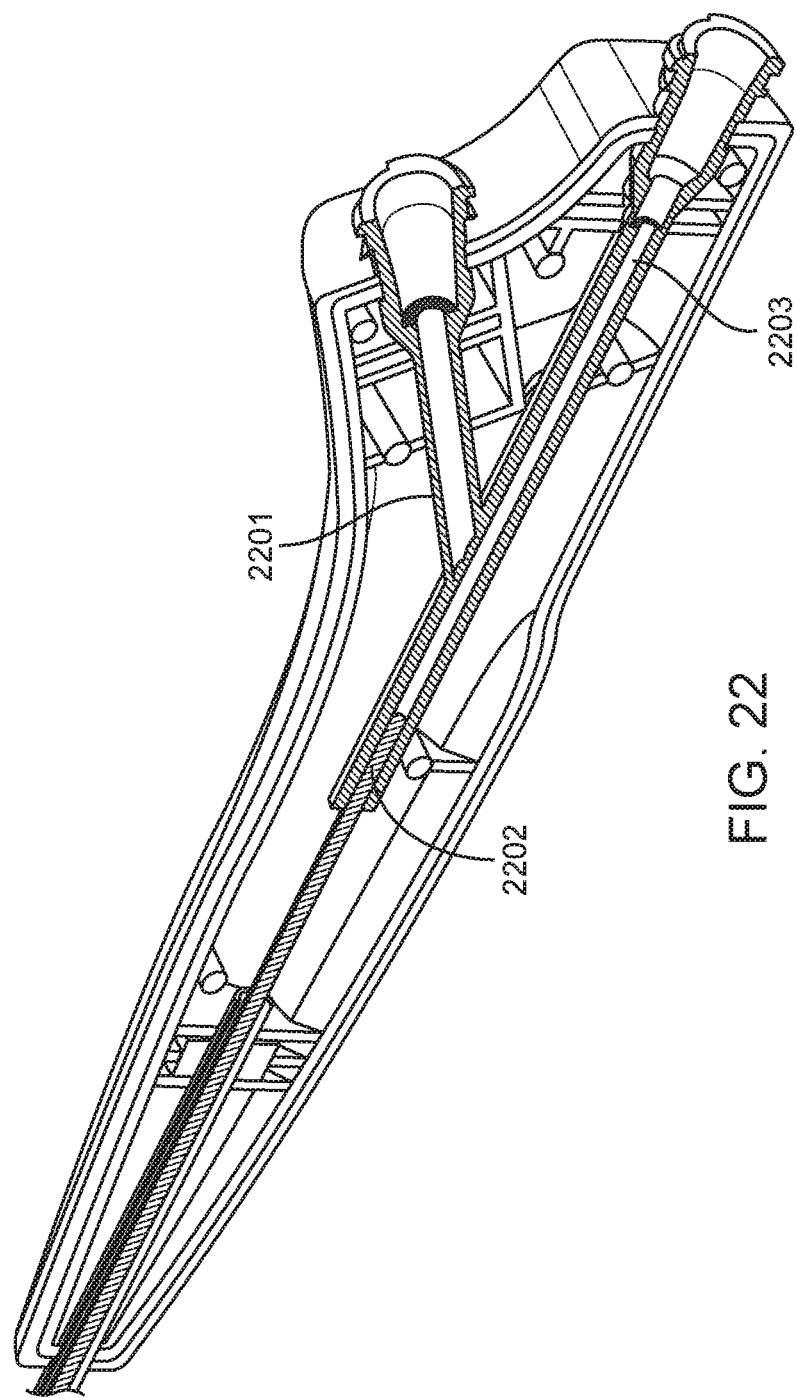
FIG. 22 shows an alternative design for terminating the contrast and therapeutic lumens utilizes in a "Y" adapter or other handle.

An alternative version of terminating the contrast and therapeutic lumens utilizes a "Y" adapter 2201, as illustrated in FIG. 22, allowing concentric therapy lumen 2202 and contrast lumen 2203 tubing configurations to be adhesively bonded directly to the "Y" adapter which terminates in luer-lock fitting for the therapeutic and contrast injection ports 901 & 903.

Figure 10:
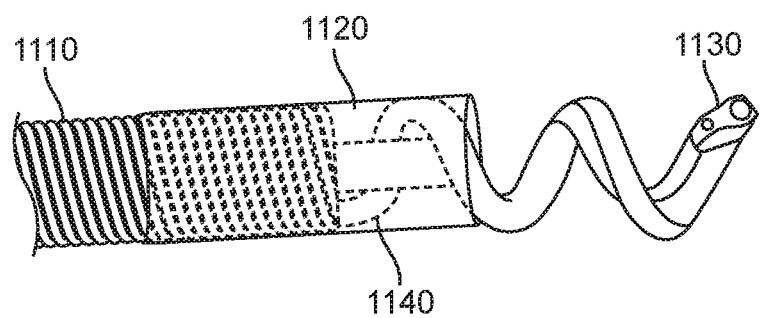
FIGS. 10 through 12B show of a distal tip of a three lumen needle injection catheter having a two lumen helical injection needle.
Figure 11:
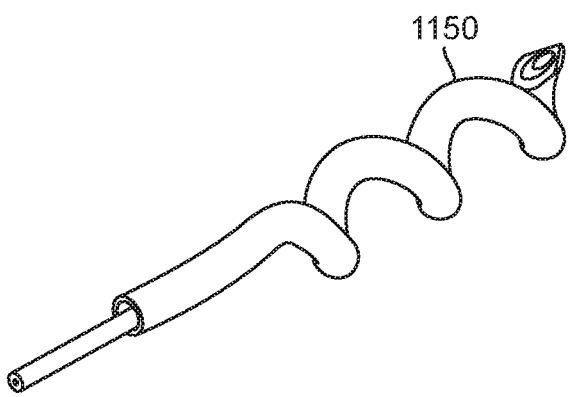
Figure 12A:
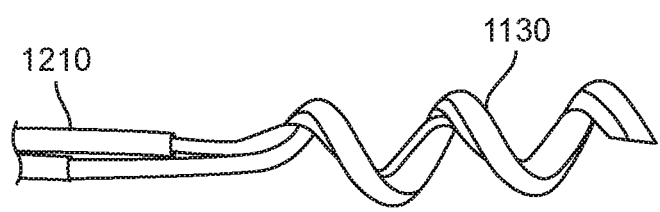
Figure 12B:
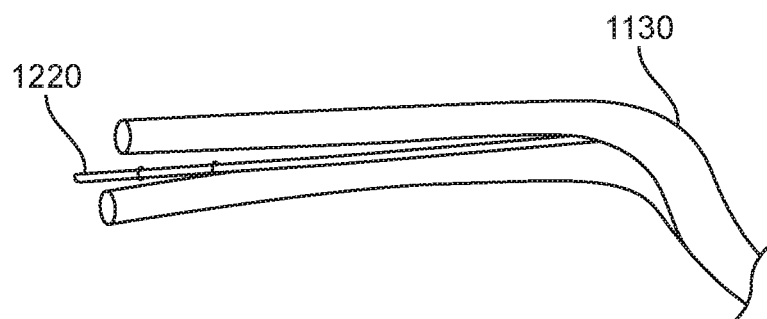

Current commercial trans-endocardial infusion system uses a helical needle made from 27RW gage 304 stainless steel hypotube (ID=0.008"). The desire to pass larger sized entities led to the development of larger helical wound hypotubes. Material and design constraints (functional requirements) were used to optimize the helix parameters of pitch, helix ID, helix OD, hypotube ID and hypo tube wall thickness. Various forming techniques were used to further optimize acceptably formed needles; for example, to control ovalization of the hypotube inside diameter. FIGS. 10 through 12 show the distal tip of a three lumen catheter with a two lumen delivery needle 1130 a contrast lumen that terminates at the base of the needle, 1120, and the flexible distal element 1110 a pentifilar coil component. All of these features are secured together as the distal tip 1140 as shown using a two part epoxy as the bonding material. The preferred embodiment for the Helix Plus needle element is a helical shaped, dual stainless steel hypotube structure 1130. For the preferred embodiment, the proximal end of both hypotubes are bonded to independent tubes 1210, that serve as the axial conduit for fluid transport. Alternate embodiments include a lumen-in-lumen design 1150 which has been described previously by Miller in U.S. Pat. No. 7,736,346. The helical needle, 1130 also serves as the distal electrode for electrophysiological sensing capabilities connected via electrode wire 12, and the exposed flexible distal element serves as the return electrode also connected by wire not shown.

Figure 13A:
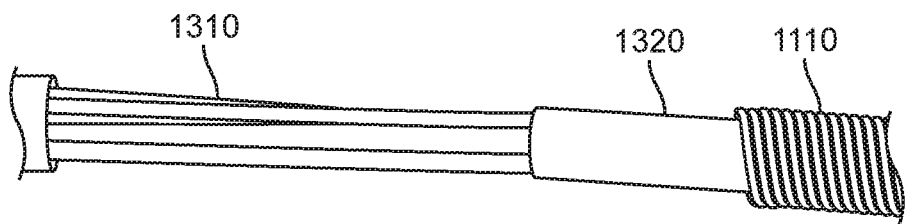
FIGS. 13A and 13B shows design and fabrication details of a tri-lumen catheter body configuration.
Figure 13B:
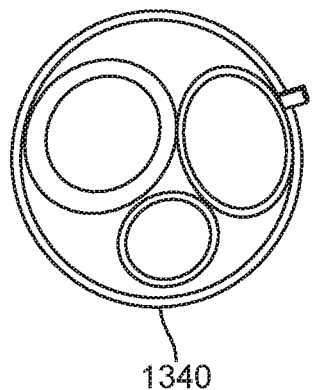

FIG. 13 shows a cross section of this tri-lumen configuration, 1340, that runs the distance of the device to the handle (electrode wires not shown). The distal and proximal electrode wires also run the length of the catheter with the tri-lumen bundle 1310 from their distal attachment points to the handle.

Figure 14A:
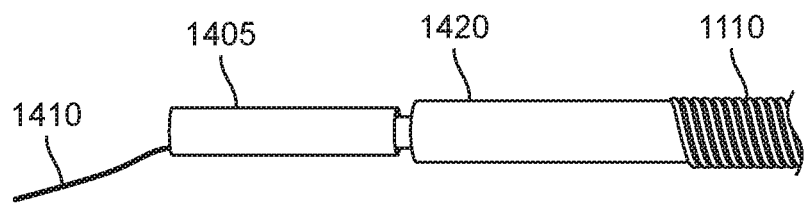
FIGS. 14A through 14C show the electrical connections of the delivery catheter in more detail.
Figure 14B:
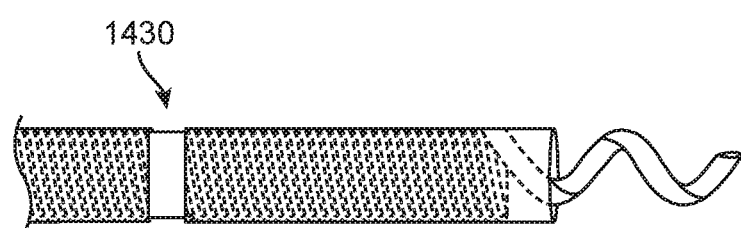
Figure 14C:
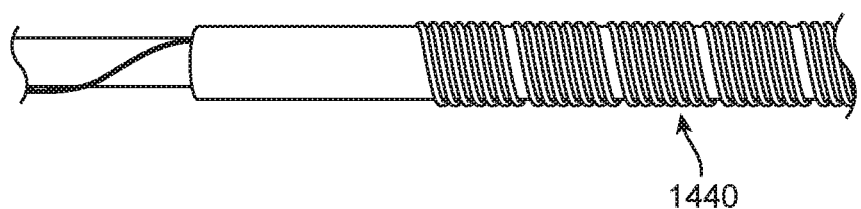

FIG. 14 shows the electrical connections of this system in more detail. The preferred design for the proximal sensing electrode to uses the distal flexible element formed of exposed pentafiler coil 1110 as the proximal electrode. An electrode wire 1410 is attached to the proximal end of the flexible element. One method of wire attachment is achieved by feeding the electrode wire through the attachment bushing 1405 winding the wire into the flexible element, 1440, and then soldered in place 1420. An alternate second electrode design uses a conductive proximal ring 1430 with the electrode wire being directed through the flexible element and attached to the ring.

Figure 15:
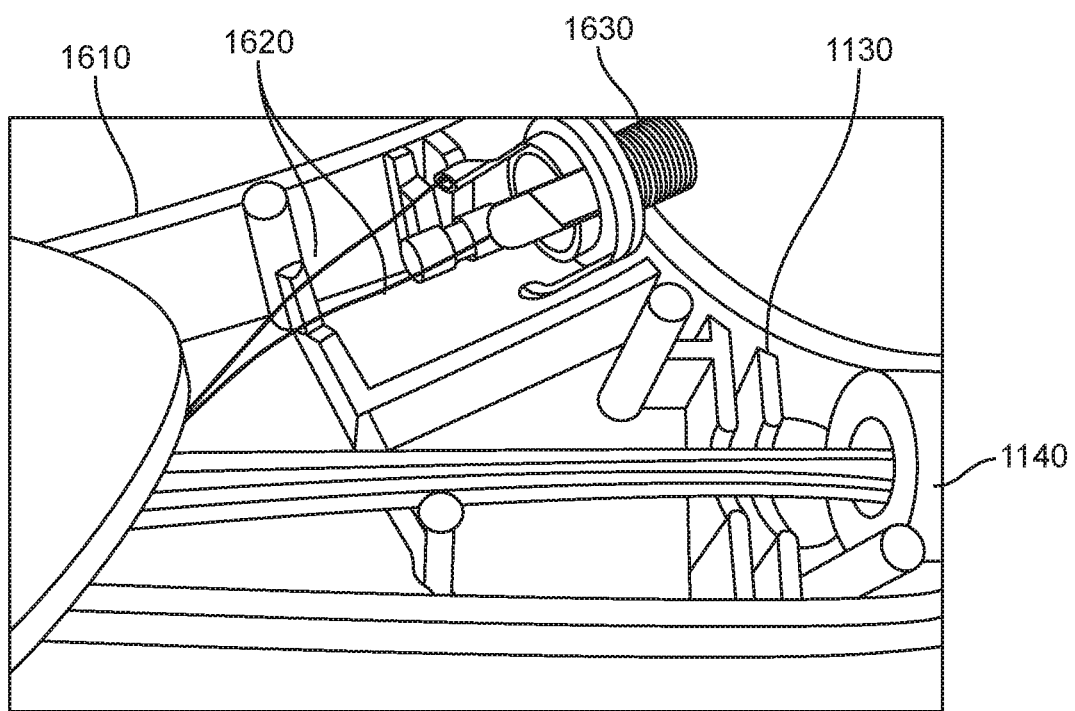
FIG. 15 shows the internal configuration of a handle assembly for the helical needle delivery catheter of the present invention.

FIG. 15 shows the internal configuration for the Helix Plus handle assembly. The following describes the proximal termination within the handle 1610 for the three liquid carrying lumens and the two electrode wires. A multi-channel electrical connector 1630 is integrated into the handle with both electrodes 1620 being connected to the component within the handle. The three lumens used for the preferred tri-lumen design are all contained within the catheter shaft, 1030 continue through the strain relief assembly 1040 and exit within the handle assembly. The individual lumens are then directed to a proximal port in the handle 1140 where they exit and connect to standard luer fittings.

Figure 16:
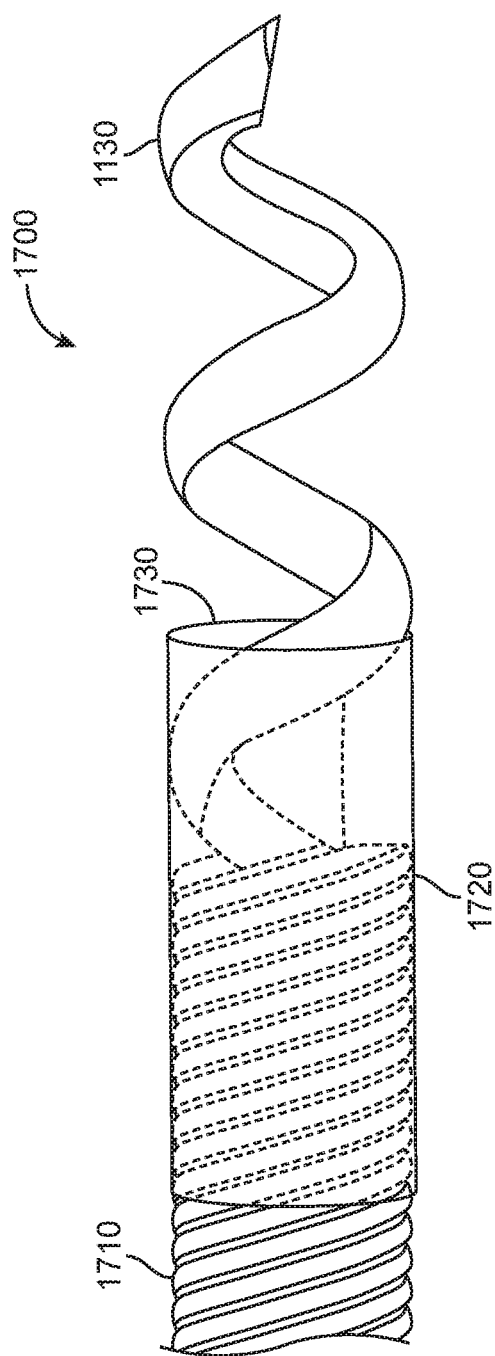
FIGS. 16 and 17 show design and fabrication details for a large bore helical needle for the delivery catheters of the present invention.
Figure 17:
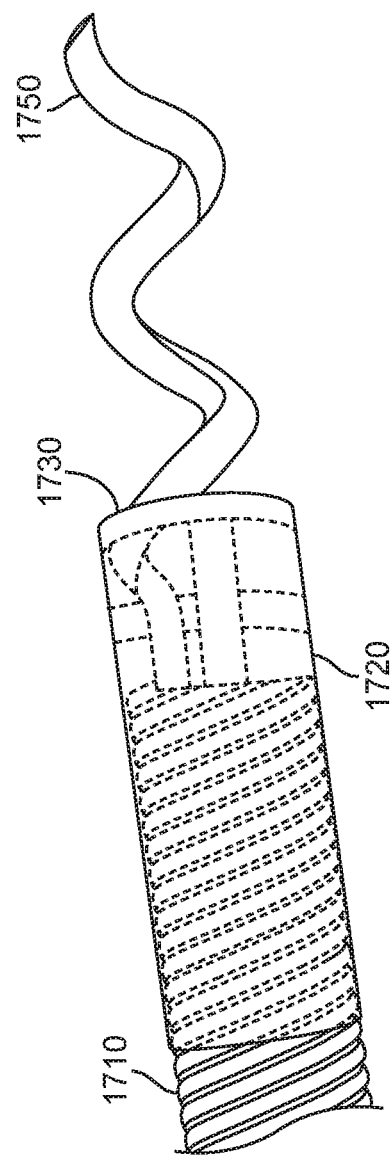

FIGS. 16 and 17 shows a large bore needle based on 23 Ga tubing 1700, and a 27RW gage helical needle 1750. The needle is secured into the tip assembly by first using UV adhesive such as Loctite 3301 to bond it into the therapeutic lumen, then secondly embedding the needle and therapeutic lumen into the pentafiler coil using in an epoxy such as Loctite M-31CL to form a unibody structure 1720 that captures a loop of the Helix. During the distal epoxy encapsulation a ribbon of PTFE is fed between the coiled loops of the needle and into the contrast lumen (adjacent to, or concentrically around the therapeutic lumen) and this PTFE ribbon creates a flow path through the epoxy when it is removed after the epoxy has cured. This contrast lumen terminates at the distal end of the embedment at the base of the exposed needle 1730. The contrast lumen can be used to assess that the tip of the shaft 805 is positioned firmly against the myocardium when a needle is screwed into tissue. This assessment is performed by injecting contrast and observing on x-ray the resulting flow and how it pools and hangs with a boundary layer against the myocardium, or if it simply flows away like a puff of smoke with the flow of the cardiac pumping.

Figure 18A:
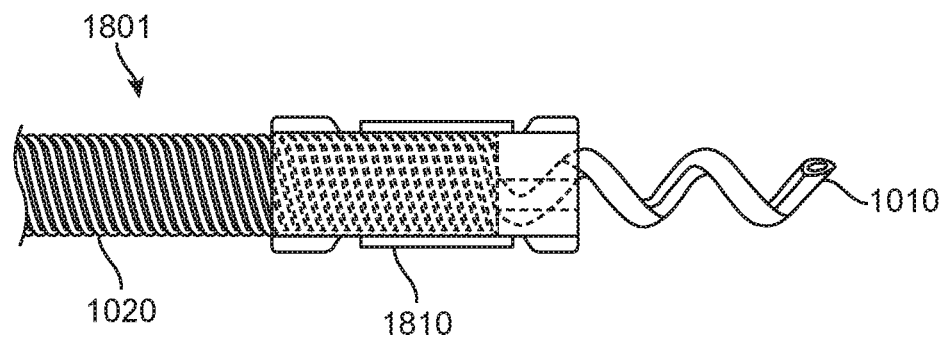
FIGS. 18A through 18C illustrate an alternate design for a penetration limit which can provide distal perforation protection utilizing existing balloon technology when engaging heart tissue during trans-endocardial therapy delivery.
Figure 18B:
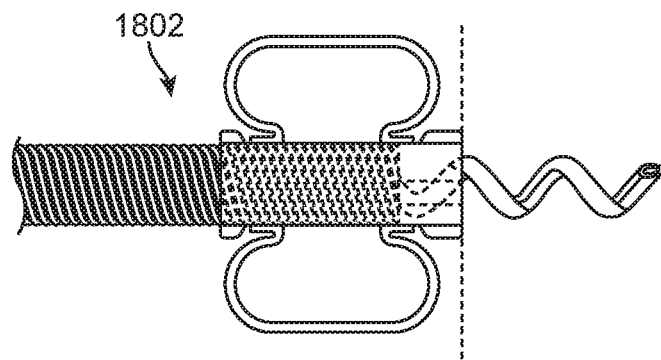
Figure 18C:
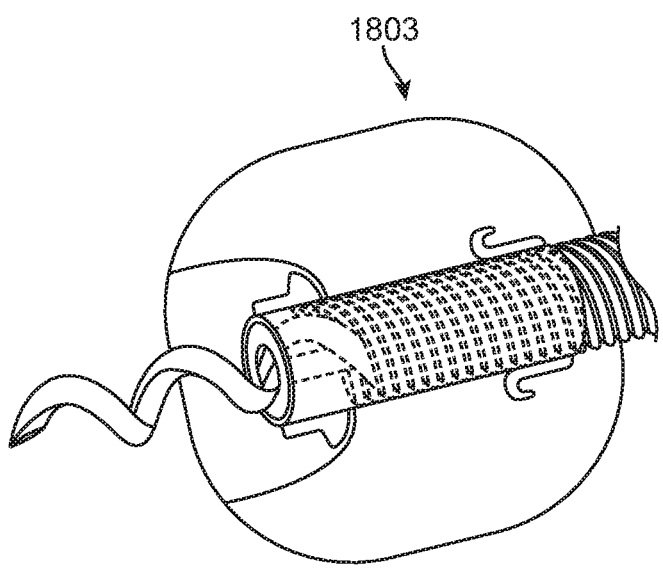

FIG. 18 shows an alternate design for distal perforation protection utilizing existing balloon technology when engaging heart tissue during trans-endocardial therapy delivery. FIG. 18 shows three different views for the distally attached balloon feature; side view in the un-inflated state 1801 the side view in the inflated state 1802 and an isometric view of the inflated state 1803. A distally attached balloon feature provides a barrier at the proximal end of the needle 1010, as shown in 1802. The preferred deployment would involve inflating the balloon, using saline or contrast medium, after it is exposed from its guide catheter and before full engagement into the heart wall. To inflate the balloon, fluid is injected in a port attached to the handle that runs through an internal lumen terminating below the surface of the balloon region in the distal end. A key advantage for this design is the ability to have a perforation protection system integrated into the distal end of the helical infusion catheter that is capable of function when rotated during standard use with a helical needle. Use of contrast as the balloon inflation medium provides the added benefit of a large radiopaque volume at the endocardial plane that can further assist with needle location and engagement assessment. A suitable balloon material, conforming to the catheter distal end in the un-inflated state 1810 is bonded at its distal and proximal ends to the base distal end structure. A port below the balloon structure connects via a suitable conduit to an inflation port in the handle.

A currently available trans-endocardial infusion systems (BioCardia, Inc.) use a helical needle made from 27RW gage 304 stainless steel hypotube (ID=0.008", OD=0.016"). The desire to use a larger lumen passing a wider range of therapeutic agents led to the development of helical wound needles utilizing larger gage tubing. Material properties constraints and the desire to maintain the smallest profile were evaluated to optimize helix needle parameters of pitch, helix ID, helix OD, hypotube ID and hypo tube wall thickness. Various forming techniques were used to further optimize acceptably formed needles; for example, to control ovalization of the hypotube inside diameter. Mandrel sizes were varied to control material deformation while trying to maintain helix diameter within constraints. Other methods of controlling excessive ovalization included freezing water in the hypotube prior to coiling, annealing the hypotube prior to coiling and side wall support during winding.

Commercial tube benders use a general rule of thumb that the bend radius of the coiled tube should not be less than two times the tube diameter, although using proprietary methods a 1:1 relationship can be achieved. Theoretical limits associated with material elongation were evaluated based on 60% elongation=0.5*Tube Diameter (TD)/Bending Radius (RB) where the % elongation limit is based on 304SS. The mandrel diameter (MD) is 2*RB−TD and the helix diameter is 2*TD+MD.

For example, a 23 gage TW 304SS hypotube with an outer diameter=0.025 in has a theoretical minimum bend radius at 60% elongation of 0.021 in (RB=(0.5*TB)/0.6). The resultant theoretical minimum mandrel diameter is 0.019 in with a helix diameter of 0.069 in. Experimental results varied from this theory as hypotubes tended to fail via ovalization versus tensile failure and the wound helix experienced "spring back" such that the final helix diameter was larger than theory.

The mandrel used to make the 23 gage TW Large Bore needles was specified to have a minor diameter of 0.018±0.002" and produced a helix outer diameter ranging from 0.071 into 0.074 in with an inner diameter of approximately 0.024 in. The "spring back" and ovalization experienced by the helix is thusly documented and demonstrates that 23 Ga TW helical needles wound on the Ø 0.018" mandrel can feasibly meet an outer diameter maximum specification.

Figure 19:
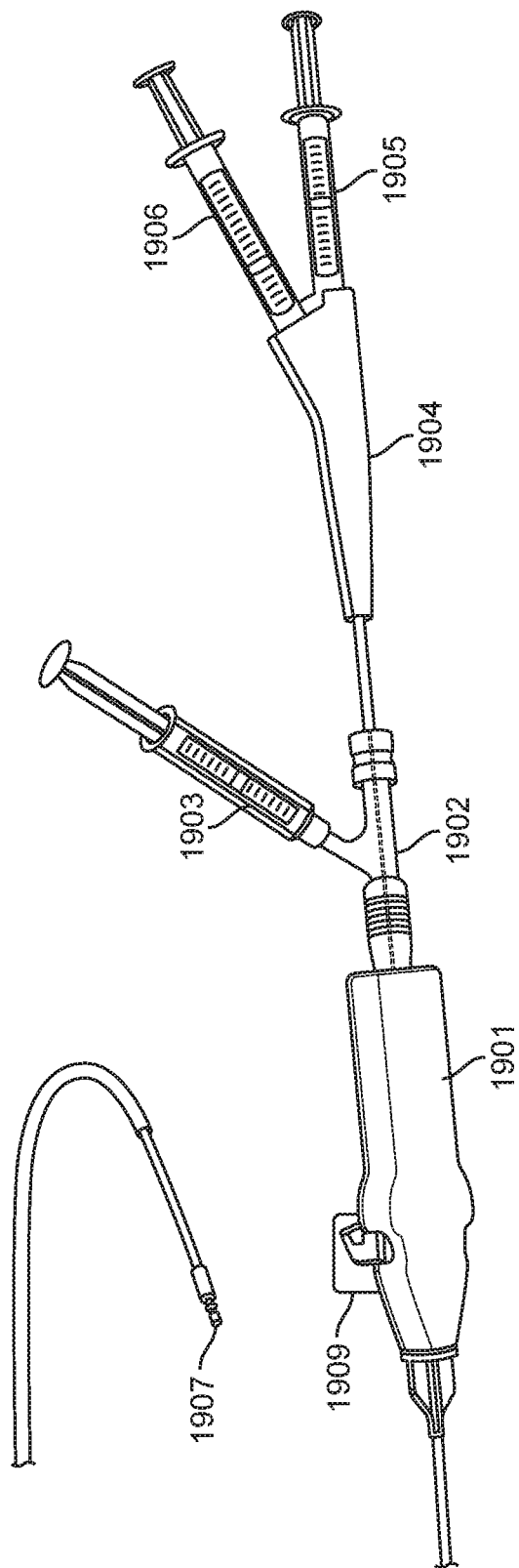
FIG. 19 shows an assembled system including a deflectable tip guide catheter having a valve, a syringe attached to a side port of the valve, a helical needle delivery catheter, a syringe attached a therapeutic port of the valve, and a syringe attached to the contrast port.

FIG. 19 shows an assembled system consisting of the following a Morph 895 deflectable tip catheter 1901 with an attached RHV (Merit MAP150) 1902, a syringe attached to the side port of the RHV 1903, a Helix catheter 1904, a syringe attached to the therapeutic port 1905, and a syringe attached to the contrast port 1906. A Helix needle at the tip 1907 is advanced and retracted through the guide to extend past the deflectable tip of the guide 1908 controlled by a guide deflection knob 1909.

Figure 20:
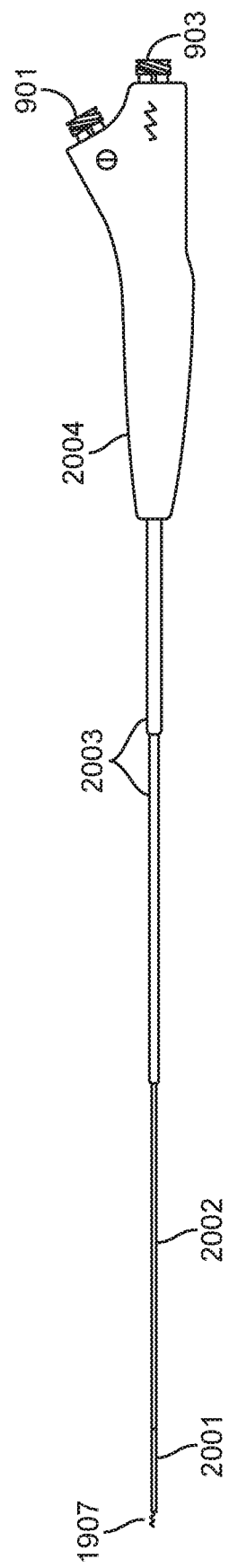
FIG. 20 illustrates a helical needle injection catheter including a helical needle, a flexible distal element, a braided shaft, two-part strain relief, a handle, a therapeutic port, and a contrast port.
Figure 21A:
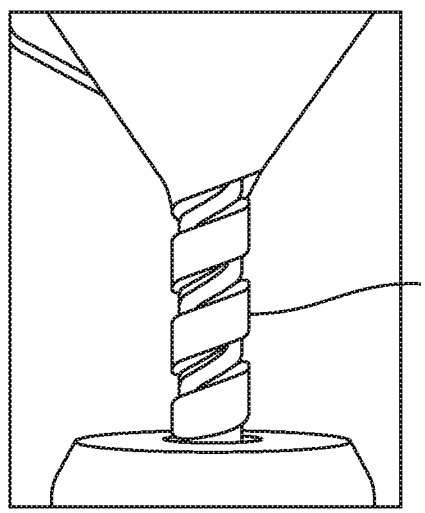
FIGS. 21A through 21D show a helical needle formed by wrapping a hypotube onto a mandrel which supports the sides of the tube to reduce deformation (ovalization).
Figure 21B:
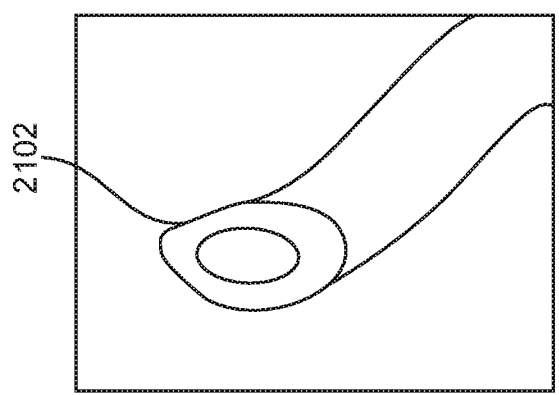
Figure 21C:
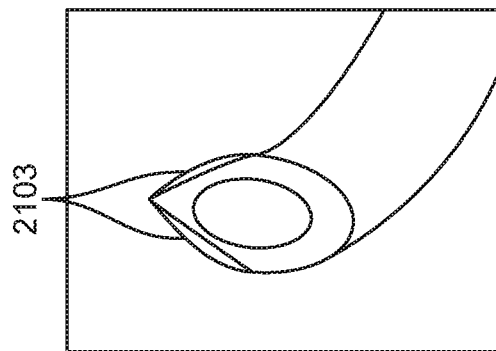
Figure 21D:
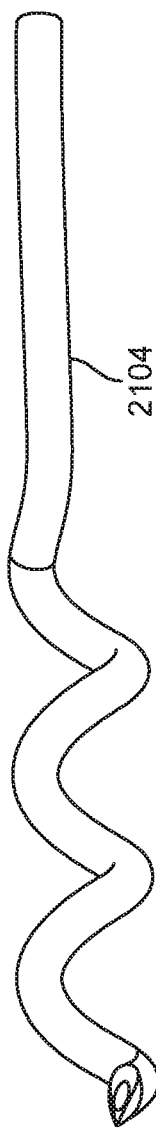

FIG. 20 shows a Helix catheter consisting of the Helical needle 1907, the flexible distal element 2001, the braided shaft 2002, the two part strain relief 2003, the handle 2004, the therapeutic port 903 and the contrast port 901.

FIGS. 21A through 21D show one method of Helix needle forming wrapping hypotube onto a mandrel 2101 which supports the sides of the tube to reduce ovalization. The needle can be formed with a variety of sized hypodermic tubing. The current commercially available iteration is made from 27 GA RW 304 stainless steel. Large bore versions have been built using 24 and 23 Ga tubing. Preferred stainless steel embodiments conform to ISO 9626 Annex A & E. Additional methods and materials to overcome limitations of material cold work limits may include forming directly to shape with electroforming of nickel or other material over a chemically removable wound mandrel such as aluminum or copper. After winding, the primary facet is cut 2102, then the secondary facets are added 2103. Additional option may include alternative tips such as closed form with side holes, trocar, or Tuohy tips. In preferred embodiments the final formed needle has a straight tail 2104 which is offset from center by an amount equal to the lumen offset in the shaft assembly, and which is bonded into the therapeutic lumen.

While the above is a complete description of the preferred embodiments of the invention, various alternatives, modifications, and equivalents may be used. Therefore, the above description should not be taken as limiting the scope of the invention, which is defined by the appended claims.

What is claimed is:

1. A method of forming a helical needle, the method comprising:
   (a) wrapping a distal portion of a hypotube onto a mandrel, the wrapped distal portion of the hypotube being in a helical configuration about a central axis of the helical distal portion when wrapped onto the mandrel;
   (b) cutting a primary facet at the distal end of the helical distal portion;
   (c) cutting at least one secondary facet at the distal end of the helical distal portion; and
   (d) forming a tail portion proximal to the helical distal portion.

2. The method of claim 1 wherein the tail axis is offset from the center axis of the helical distal portion.

3. The method of claim 1 wherein the primary face is substantially perpendicular to a plane coincident with the central plane of the catheter shaft.

4. The method of claim 1, further comprising cutting one or more side holes into the hypotube.

5. The method of claim 1, wherein the hypotube is formed of stainless steel.

6. The method of claim 1, wherein the hypotube has a gauge of 23 to 32.

7. The method of claim 1, wherein the primary facet is formed perpendicular to a plane coincident with the tail axis and the center axis of the helical distal portion.

8. The method of claim 1, wherein cutting at least one secondary facet comprises cutting a first secondary facet and a second secondary facet at the distal end of the helical portion.

9. The method of claim 8, wherein the first and second secondary facets are symmetrical about a distal point of the first facet.

10. The method of claim 1, wherein the tail portion is straight.

11. The method of claim 1, wherein cutting the primary and secondary facets at the distal end of the helical distal portion forms the distal end into a sharp distal tip.

12. The method of claim 1, wherein the hypotube has at least one lumen open at the distal end of the helical distal portion.

13. A helical needle comprising a hypotube having:
   (a) a tail portion having an axis of symmetry;
   (b) a helical portion, wherein a center axis of the helical portion is offset from the axis of symmetry, and wherein a distal end of the helical portion comprises a primary facet and at least one secondary facet.

14. The helical needle of claim 13, wherein the hypotube has one or more side holes.

15. The helical needle of claim 13, wherein the hypotube is formed of stainless steel.

16. The helical needle of claim 13, wherein the hypotube has a gauge of 23 to 32.

17. The helical needle of claim 13, wherein the primary facet is perpendicular to a plane coincident with the tail axis and the center axis of the helical portion.

18. The helical needle of claim 13, wherein the at least one secondary facet of the distal end of the helical portion comprises a first secondary facet and a second secondary facet.

19. The helical needle of claim 18, wherein the first and second secondary facets are symmetrical about a distal point of the first facet.

20. The helical needle of claim 13, wherein the tail portion is straight.

21. The helical needle of claim 13, wherein the distal end of the helical portion comprises a sharp distal tip.

22. The helical needle of claim 13, wherein the hypotube has at least one lumen open at the distal end of the helical distal portion.

23. A catheter for infusing fluids to a heart of a patient, the catheter comprising a hollow hypotube having a helical portion and a tail portion, wherein a tip of the helical portion of the hypotube has two or more facets.

24. The catheter of claim 23, wherein the hollow hypotube comprises a first portion and a second portion coupled to the first portion.

25. The catheter of claim 23, wherein the hollow hypotube comprises a first electrode coupling configured to couple to a first electrode wire.

26. The catheter of claim 25, wherein the hollow hypotube further comprises a second electrode coupling configured to couple to a second electrode wire.

27. The catheter of claim 26, wherein the helical portion comprises second electrode coupling.

28. The catheter of claim 23, wherein the tip of the helical portion of the hypotube has two or more facets cut after the winding of the helical portion.

29. The catheter of claim 23, wherein the tip of the helical portion of the hypotube has a primary facet formed perpendicular to a plane coincident with the center axis of the helical portion.

* * * * *